United States Patent
Okazaki et al.

[11] Patent Number: 5,993,641
[45] Date of Patent: Nov. 30, 1999

[54] AIR FUEL RATIO DETECTION USING CURRENT-LIMITED SENSOR WITH DIFFERENT TIMING AND/OR MAGNITUDE OF INCREMENTAL CHANGES IN APPLIED SENSOR VOLTAGE

[75] Inventors: Kazuhiro Okazaki, Anjo; Satoshi Haseda, Okazaki; Koji Jono, Anjo; Masayuki Takami, Kariya; Tomomichi Mizoguchi, Nagoya, all of Japan

[73] Assignee: Denso Corporaton, Kariya, Japan

[21] Appl. No.: 08/996,885

[22] Filed: Dec. 23, 1997

[30] Foreign Application Priority Data

Dec. 24, 1996 [JP] Japan ................................. 8-343774

[51] Int. Cl.$^6$ ............................. G01F 1/64; G01N 17/00; G01N 27/26
[52] U.S. Cl. .................. 205/784.5; 204/424; 204/425; 204/428
[58] Field of Search ................................. 205/783.5, 784, 205/784.5, 785; 204/425, 426, 428, 424

[56] References Cited

U.S. PATENT DOCUMENTS

| | | |
|---|---|---|
| 4,534,330 | 8/1985 | Osuga et al. ............................. 123/440 |
| 4,553,424 | 11/1985 | Sakurai et al. . |
| 4,658,790 | 4/1987 | Kitahara ................................... 204/425 |
| 4,664,773 | 5/1987 | Suzuki et al. . |
| 4,707,241 | 11/1987 | Nakagawa et al. ..................... 204/406 |
| 4,882,030 | 11/1989 | Suzuki et al. . |

FOREIGN PATENT DOCUMENTS

| | | |
|---|---|---|
| 61-237047 | 10/1986 | Japan . |
| 61-280560 | 12/1986 | Japan . |
| 61-296260 | 12/1986 | Japan . |
| 2-27255 | 1/1990 | Japan . |
| 2-45751 | 2/1990 | Japan . |
| 2-99852 | 4/1990 | Japan . |

*Primary Examiner*—Robert J. Warden, Sr.
*Assistant Examiner*—Kaj K. Olsen
*Attorney, Agent, or Firm*—Nixon & Vanderhye P.C.

[57] ABSTRACT

An A/F sensor outputs a linear air-fuel ratio detection signal proportional to the oxygen concentration in an exhaust gas from an engine upon application of a voltage. A computer controls the applied-voltage in a stoichiometric control region, a lean burn control region, an atmosphere detection region and a rich control region to have a fixed value such that the change rate of the applied-voltage is reduced to be less than that in other regions. In addition, when changing the voltage applied to the A/F sensor, the computer variably sets the voltage change speed sequentially. Thus, the influence of the capacitive characteristic of the A/F sensor is eliminated.

18 Claims, 18 Drawing Sheets

AIR FUEL RATIO DETECTION USING CURRENT-LIMITED SENSOR WITH DIFFERENT TIMING AND/OR MAGNITUDE OF INCREMENTAL CHANGES IN APPLIED SENSOR VOLTAGE

CROSS REFERENCE TO RELATED APPLICATION

This application relates to and incorporates herein by reference Japanese Patent Application No. 8-343774 filed on Dec. 24, 1996.

BACKGROUND OF THE INVENTION

1. Field of the Invention

The present invention relates to air-fuel ratio detection using a current limited (limit-current) type air-fuel ratio sensor which outputs a current signal corresponding to an air-fuel ratio in a detection object gas upon application of a voltage to the sensor.

2. Related Art

In recent years, in air-fuel ratio control for vehicle engines, there are needs for increased control precision and lean burning. To respond to these needs, a linear air-fuel ratio sensor which widely and linearly detects the air-fuel ratio of the gaseous mixture (oxygen concentration in an exhaust gas) supplied into an engine, and an air-fuel ratio detecting apparatus using this sensor are employed. As such air-fuel ratio sensor, in a limit-current air-fuel ratio sensor, its limit-current detection region shifts in accordance with an air-fuel ratio (oxygen concentration), as it is well known. More specifically, in the known V-I characteristic graph, the limit-current detection region comprises a linear segment parallel to the axis V, and the region shifts to the positive voltage side as the air-fuel ratio moves toward the lean side, while it shifts to the negative voltage side as the air-fuel ratio moves toward the rich side. Accordingly, if a voltage applied to the sensor has a fixed value when the air-fuel ratio changes, it is impossible to perform precise air-fuel ratio detection using the limit-current detection region (the linear segment parallel to the axis V) in the entire air-fuel ratio detection range.

Accordingly, a technique to variably set a voltage applied to the air-fuel ratio sensor in accordance with the air-fuel ratio (sensor current) is desired. As this type of prior art, Japanese Patent Publication No. 7-18837 discloses "air-fuel ratio detecting apparatus" which instantly cuts off the voltage applied to the air-fuel ratio sensor to detect sensing element internal-resistance from an electromotive force and current at that time, and variably sets the applied-voltage based on the sensing element internal-resistance. Further, the "air-fuel ratio sensor" disclosed in Japanese Patent No. 2509905 uses a technique to stepwise change an applied-voltage in accordance with whether the air-fuel ratio is on the rich side or the lean side.

However, since a zirconia sensor, which is generally used as a linear air-fuel ratio sensor, has a capacitive (condenser) characteristic, the above conventional techniques cause the following problem. FIG. 27 shows an equivalent circuit of the air-fuel ratio sensor. In the equivalent circuit, reference symbol Rg denotes a particle resistance of solid electrolyte (zirconia sensing element) with respect to oxygen ions; Rh and Ch, respectively a boundary resistance and a boundary capacitance of the surface of the particle of the solid electrolyte; Rf and Cf, respectively an electrode surface resistance and an electrode surface capacitance. In this case, as shown in FIG. 28, when the voltage applied to the air-fuel ratio sensor is changed, the current of the sensor causes a peak current immediately after voltage change due to the influence of electric charge on the above values Ch, Cf, which, as a result, prolongs the time required until the current converges into a predetermined current value.

This situation is especially regarded as a serious problem for realizing high-precision air-fuel ratio feedback control, however, the techniques disclosed in the above publications have not solved this problem. As a result, in a region, where an air-fuel ratio should be detected with high precision, such as a stoichiometric control region (a region having air-fuel ratio=about 13 to 17), air-fuel ratio detection precision is degraded, and further, air-fuel ratio control precision might be lowered to cause inconveniences such as degradation of emission.

SUMMARY OF THE INVENTION

It is an object of the present invention to overcome the above drawbacks.

It is a further object of the present invention to improve air-fuel ratio detection precision while widely detecting the air-fuel ratio.

According to one aspect of the present invention, the change rate of a voltage applied to an air-fuel ratio sensor in at least one specific region is reduced to be smaller than that in other regions. Preferably, the specific region includes a stoichiometric ratio peripheral region and, more preferably, includes a lean air-fuel ratio region, rich air-fuel ratio region or atmosphere detection region. Preferably, the applied-voltage in this region is fixed. Preferably, the region is varied in accordance with the internal-resistance of the air-fuel ratio sensor.

Further, according to another aspect of the present invention, the voltage change speed is varied by a voltage width or time period, or both, when the applied-voltage is changed from one to another. Preferably, the applied-voltage change speed is set in accordance with the difference between a target voltage and an actual applied-voltage, the internal-resistance of the air-fuel ratio sensor, the change amount of the current value detected by the air-fuel ratio sensor, a present value of the applied-voltage, the slope of the applied-voltage characteristic line (change rate of the applied-voltage) on voltage-current characteristic of the air-fuel ratio sensor, or the like.

BRIEF DESCRIPTION OF THE DRAWINGS

Other objects, features and advantages of the present invention will become more apparent from the following detailed description when read with reference to the accompanying drawings. In the drawings.

DETAILED DESCRIPTION OF THE PREFERRED EMBODIMENTS

An air-fuel ratio detecting apparatus is implemented in an air-fuel feedback control system according to various embodiments of the present invention. The apparatus is applied to an electronically-controlled gasoline injection engine mounted on a vehicle. The apparatus controls a fuel injection amount to the engine to a desired air-fuel ratio based on the result of detection by an air-fuel ratio sensor. In the following description, the procedure of detecting the air-fuel (A/F) ratio using the air-fuel ratio sensor and feedback control procedure based on the result of detection by the sensor will be described in detail.

(First Embodiment)

Figure 1:
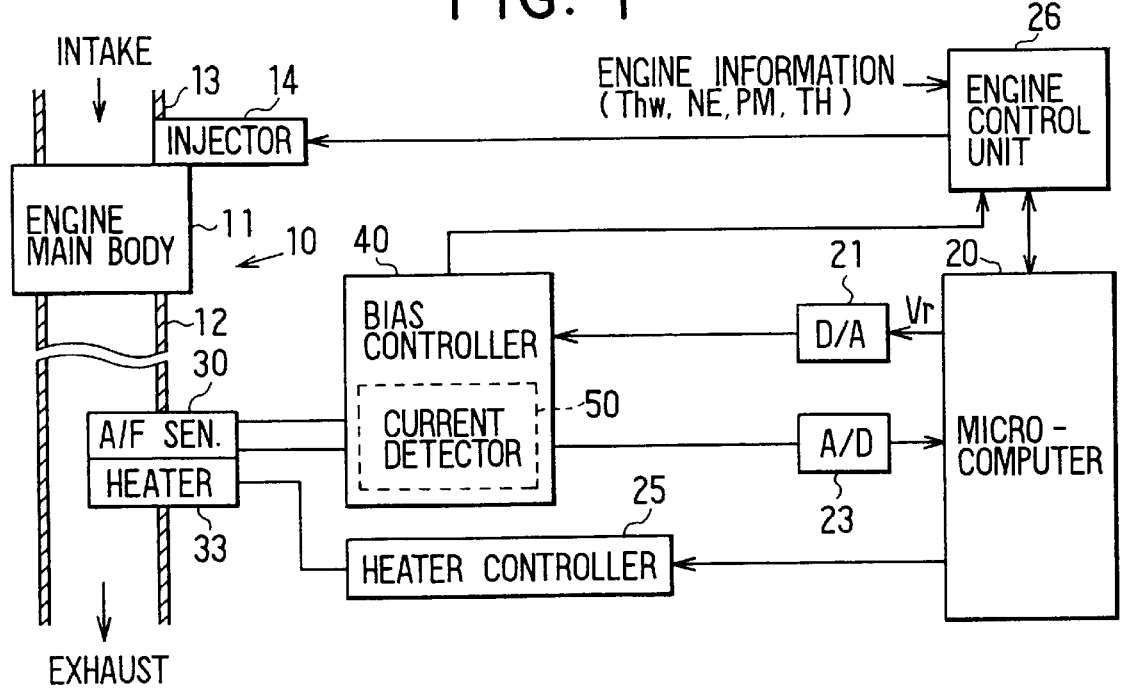
FIG. 1 is a block diagram showing a schematic construction of an air-fuel ratio feedback control apparatus according to the first embodiment.

In FIG. 1 showing the schematic construction of the air-fuel ratio feedback control apparatus according to the present embodiment, the air-fuel ratio feedback control apparatus comprises a limit-current air-fuel ratio sensor (hereinafter referred to as "A/F sensor") 30. The A/F sensor 30 is attached to an exhaust pipe 12 extending from an engine main body 11 of an engine 10. The A/F sensor 30 outputs a linear air-fuel ratio detection signal proportional to an oxygen concentration in an exhaust gas, upon application of a voltage instructed from a microcomputer 20. The microcomputer 20 comprises a conventional well-known CPU for executing various calculation processing, ROM, RAM and the like. The microcomputer 20 controls a bias controller 40 and a heater controller 25 to be described later, in accordance with predetermined control programs.

Further, an injector 14 of electromagnetic driving type is provided at the downstream portion of an intake pipe 13 of the engine main body 11. The injector 14 opens its valve by a drive instruction from an engine control unit (ECU) 26, and injects fuel to respective cylinders of the engine main body 11. The ECU 26 inputs an engine water temperature Thw, an engine speed NE, an intake pressure PM, a throttle opening TH and the like, as engine information.

Figure 2:
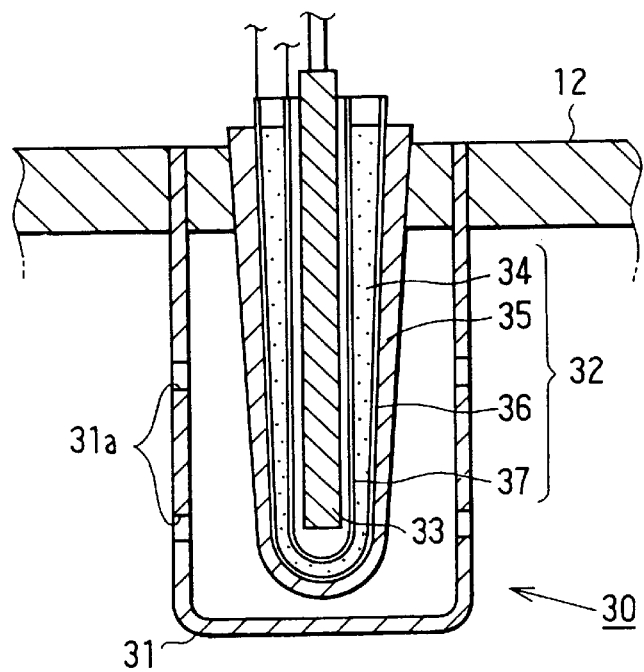
FIG. 2 is a cross-sectional view showing the detailed structure of an A/F sensor used in the first embodiment.

FIG. 2 is a cross sectional view showing the schematic structure of the A/F sensor 30. In FIG. 2, the A/F sensor 30 protrudes toward the inside of the exhaust pipe 12, and the A/F sensor 30 generally comprises a cover 31, a sensor main body 32 and a heater 33. The cover 31 has a U-shaped cross section, and has a number of small holes 31a communicating the inside and the outside of the cover, around the peripheral wall of the cover. The sensor main body 32 generates a limit-current corresponding to the oxygen concentration in a lean region of an air-fuel ratio or unburned gas (CO, HC, $H_2$ and the like) concentration in a rich region of the air-fuel ratio.

The construction of the sensor main body 32 will be described. In the sensor main body 32, an exhaust-gas-side electrode layer 36 is fixed on the outer surface of a solid electrolyte layer 34 formed to have a cup-shaped cross section, and an atmosphere-side electrode layer 37 is fixed on the inner surface of the solid electrolyte layer 34. Further, a diffused-resistor layer 35 is formed by plasma coating or the like, on the outer surface of the exhaust-gas-side electrode layer 36. The solid electrolyte layer 34 comprises an oxygen ion-conductive oxide sintered material using solidified $ZrO_2$, $HfO_2$, $ThO_2$, $Bi_2O_3$ and the like with CaO, MgO, $Y_2O_3$, $Yb_2O_3$ and the like being used as stabilizers. The diffused-resistor layer 35 comprises a thermally resistant inorganic material such as alumina, magnesia, silica stone, spinel and mullite. The exhaust-gas-side electrode layer 36 and the atmosphere-side electrode layer 37 both comprise a noble metal such as platinum having a high catalytic activity, and their surfaces are plated with a porous chemical. The area and the thickness of the exhaust-gas-side electrode layer 36 are 10–100 $mm^2$ (square millimeter) and about 0.5–2.0 $\mu m$, on the other hand, the area and the thickness of the atmosphere-side electrode layer 37 are 10 $mm^2$ (square millimeter) or greater and about 0.5–2.0 $\mu m$.

The heater 33 is contained in the atmosphere-side electrode layer 37, and heats the sensor main body 32 (the atmosphere-side electrode layer 37, the solid electrolyte layer 34, the exhaust-gas-side electrode layer 36 and the diffused-resistor layer 35) by its heating energy. The heater 33 has a sufficient heating capacity to activate the sensor main body 32.

In the A/F sensor 30 having the above construction, the sensor main body 32 generates a limit-current corresponding to the oxygen concentration in a lean region from a stoichiometric ratio point. In this case, the limit-current corresponding to the oxygen concentration is determined by the region of the exhaust-gas-side electrode layer 36, the thickness of the diffused-resistor layer 35, a porosity and an average hole diameter. Further, the sensor main body 32 detects the oxygen concentration by a linear characteristic. To activate the sensor main body 32, about 600° C. or higher temperature is required, and as the active temperature range of the sensor main body 32 is narrow, the active region cannot be controlled only by heating with exhaust gas from the engine 10. For this reason, in the present embodiment, the sensor main body 32 is heated to the active temperature range by heating control of the heater 33. In a region on the rich side from the stoichiometric air-fuel ratio, the concentration of carbon monoxide (CO) and the like as unburned gases varies substantially linearly with respect to the air-fuel ratio, and the sensor main body 32 generates a limit-current corresponding to the concentration of CO and the like.

Figure 3:
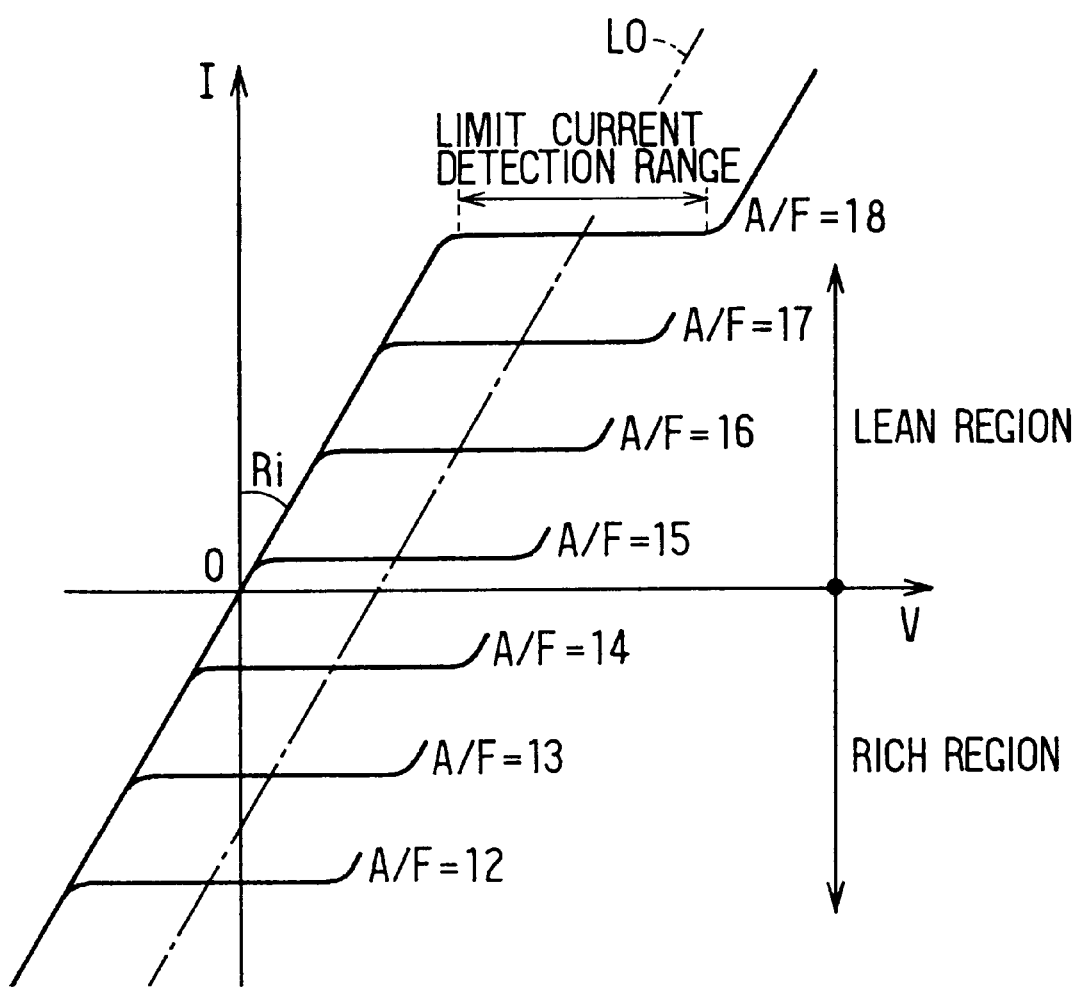
FIG. 3 is a V-I characteristic diagram of the A/F sensor.

The voltage-current characteristic of the sensor main body 32 will be described with reference to FIG. 3. It is understood from FIG. 3 that a current which flows into the solid electrolyte layer 34 of the sensor main body 32 in proportion to the air-fuel ratio detected by the A/F sensor 34 and the voltage applied to the solid electrolyte layer 34 respectively have a linear characteristic. In this case, the linear segment parallel to the voltage axis V defines the limit-current of the sensor main body 32. The increment/decrement of the limit-current (sensor current) corresponds to the increment/decrement of the air-fuel ratio (i.e., lean/rich). That is, as the air-fuel ratio approaches to the lean side, the limit-current increases, while the air-fuel ratio approaches to the rich side, the limit-current decreases.

Further, in this voltage-current characteristic, a region having a voltage less than that of the straight line segment parallel to the voltage axis V is a resistance dominant region. The slope of a linear segment in the resistance dominant region is defined by the internal-resistance of the solid electrolyte layer 34 in the sensor main body 32. Since the sensing element internal-resistance varies in accordance with temperature change, as the temperature of the sensor main body 32 decreases, the slope becomes small due to increase in the sensing element internal-resistance.

On the other hand, a bias command signal (digital signal) Vr for application of a voltage to the A/F sensor 30 is inputted into a D/A converter 21 from the microcomputer 20, converted into an analog signal Vb by the D/A converter 21, and inputted into a bias controller 40 for application of an air-fuel ratio detection voltage to the A/F sensor 30. At this time, upon air-fuel ratio detection, generally, a characteristic line L0 in FIG. 3 is used to set a voltage corresponding to the air-fuel ratio at that time (sensor current value).

Further, the bias controller 40 detects the value of current that flows upon application of the voltage to the A/F sensor 30 by a current detector 50. The analog signal of the current value detected by the current detector 50 is inputted into the microcomputer 20 via an A/D converter 23. The detailed construction of the bias controller 40 will be described later. The heater 33 provided at the A/F sensor 30 operates under the control of the heater controller 25. That is, the heater controller 25 duty-controls electric power supplied from a battery-power source (not shown) to the heater 33 in accordance with the sensing element temperature of the A/F sensor 30 or the temperature of the heater, thus controlling heating of the heater 33.

Figure 4:
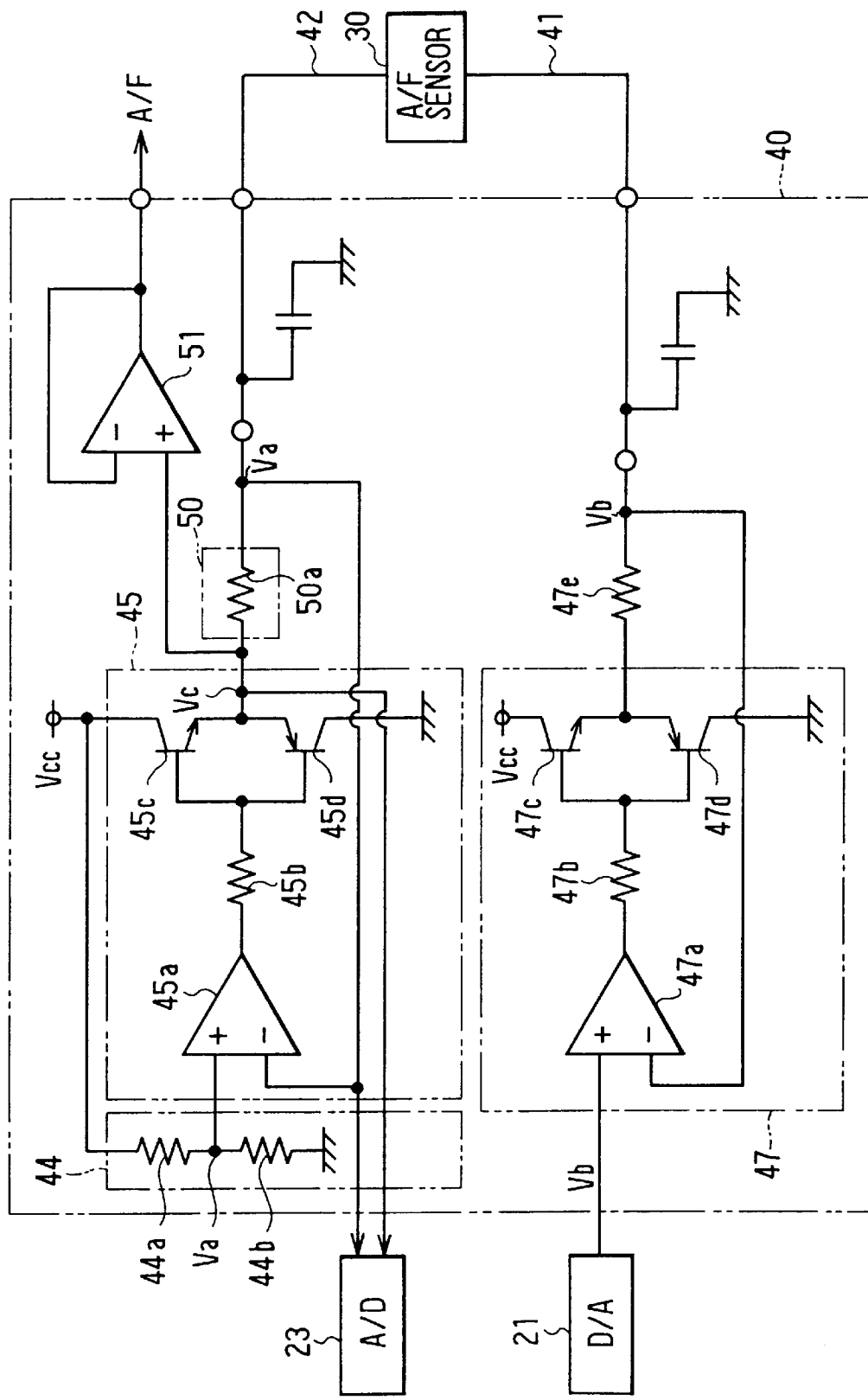
FIG. 4 is an electric circuit diagram showing the construction of a bias controller used in the first embodiment.

Next, the construction of the bias controller 40 will be described with reference to an electric circuit diagram of FIG. 4. In FIG. 4, the bias controller 40 generally comprises a reference voltage circuit 44, a first voltage supply circuit 45, a second voltage supply circuit 47 and the current detector 50. The reference voltage circuit 44 divides a constant voltage Vcc by voltage dividing resistors 44a and 44b so as to generate a constant reference voltage Va.

The first voltage supply circuit 45, comprising a voltage follower circuit, supplies a voltage Va equivalent to the reference voltage Va of the reference voltage circuit 44 to one terminal 42 of the A/F sensor 30 (the terminal 42 is connected to the atmosphere-side electrode layer 37 in FIG. 2). More specifically, the first voltage supply circuit 45 comprises an operational amplifier 45a having a positive-side input terminal connected to a voltage dividing point of the respective voltage dividing resistors 44a and 44b and a negative-side input terminal connected to one terminal 42 of the A/F sensor 30, a resistor 45b having one end connected to an output terminal of the operational amplifier 45a, and a NPN transistor 45c and an PNP transistor 45d respectively having a base connected to the other terminal of the resistor 45b. The collector of the NPN transistor 45c is connected to the constant voltage Vcc, and the emitter is connected to one terminal of the A/F sensor 30 via a current detection resistor 50a constituting the current detector 50. Further, the emitter of the PNP transistor 45d is connected to the emitter of the NPN transistor 45c, and the collector is grounded.

The second voltage supply circuit 47, also comprising a voltage follower circuit, supplies a voltage Vb equivalent to the reference voltage Vb of the D/A converter 21 to one terminal 41 of the A/F sensor 30 (the terminal 41 is connected to the exhaust-gas-side electrode layer 36 in FIG. 2). More specifically, the second voltage supply circuit 47 comprises an operational amplifier 47a having a positive-side input terminal connected to an output of the D/A converter 21 and a negative-side input terminal connected to the other terminal 41 of the A/F sensor 30, a resistor 47b having one end connected to an output terminal of the operational amplifier 47a, and a NPN transistor 47c and an PNP transistor 47d respectively having a base connected to the other terminal of the resistor 47b. The collector of the NPN transistor 47c is connected to the constant voltage Vcc, and the emitter is connected to the other terminal of the A/F sensor 30 via a resistor 47e. Further, the emitter of the PNP transistor 47d is connected to the emitter of the NPN transistor 47c, and the collector is grounded.

By the above construction, the reference voltage Va is always supplied to the one terminal 42 of the A/F sensor 30. If the voltage Vb supplied to the other terminal 41 of the A/F sensor 30 via the D/A converter 21 is lower than the reference voltage Va (Vb<Va), the A/F sensor 30 is positively biased. Further, if the voltage Vb supplied to the other terminal 41 of the A/F sensor 30 via the D/A converter 21 is higher than the reference voltage Va (Vb>Va), the A/F sensor 30 is negatively biased. In this case, the sensor current (limit-current) that flows upon application of the voltage is detected as a potential difference between both terminals of the current detection resistor 50a, and inputted into the microcomputer 20 via the A/D converter 23.

Further, an output buffer 51 is connected to the current detector 50. The air-fuel ratio (A/F) detected by the A/F sensor 30 is directly outputted as a voltage signal by the output buffer 51.

Next, the operation of the air-fuel ratio feedback control apparatus having the above construction will be described.

Figure 5:
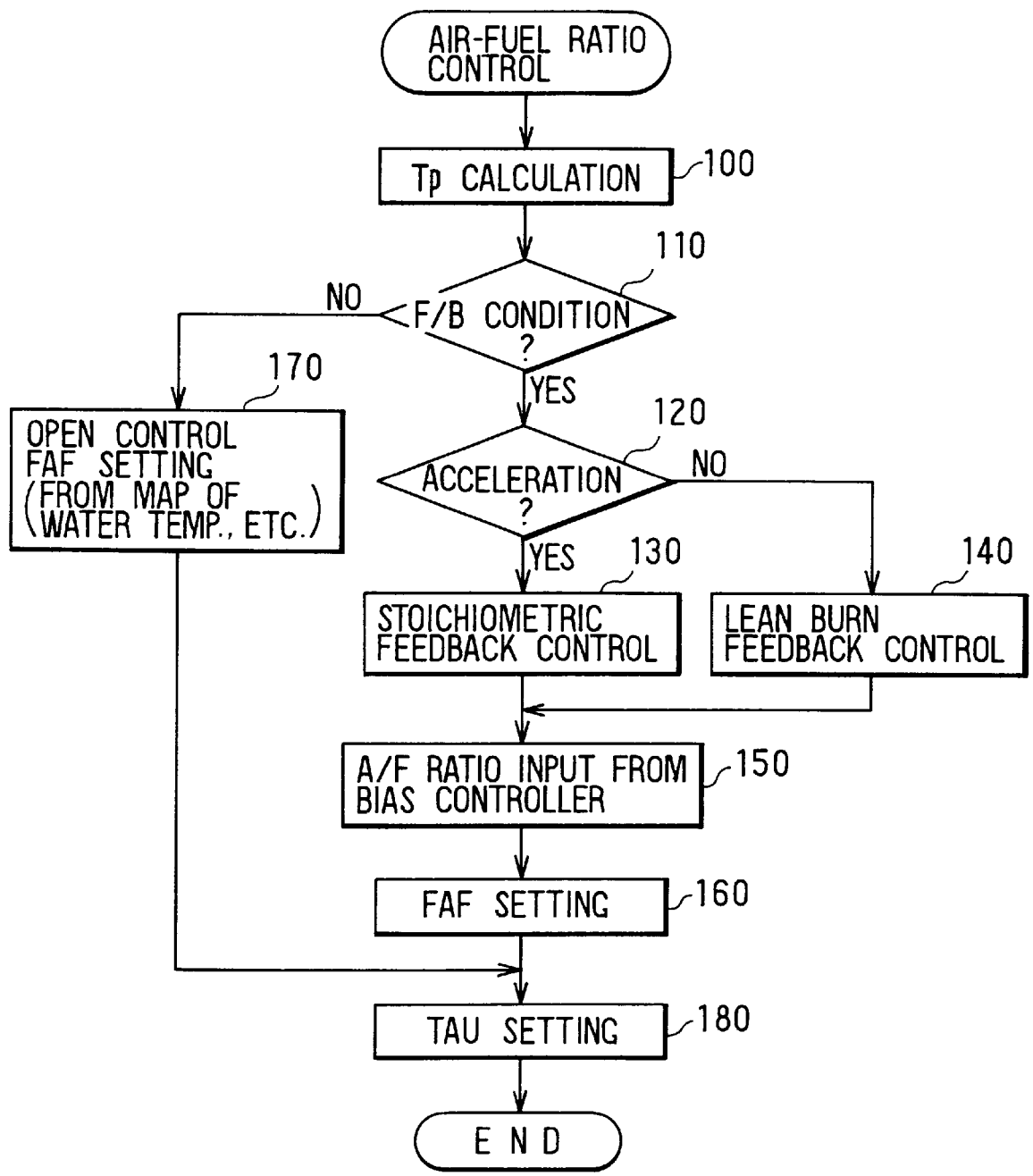
FIG. 5 is a flowchart showing an air-fuel ratio control routine in the first embodiment.

FIG. 5 is a flowchart showing an air-fuel ratio control routine according to the present embodiment. The flowchart is executed by the engine control unit ECU (hereinafter abbreviated to "ECU") 26 in synchronization with fuel injection by the injector 14. In the present embodiment, as air-fuel ratio control, open control, stoichiometric F/B control or lean burn F/B control is selected in accordance with engine driving condition. Especially, the stoichiometric F/B control performs F/B control in accordance with the difference between a stoichiometric ratio (A/F=14.7) as a target air-fuel ratio and an actual air-fuel ratio at that time, and the lean burn F/B control performs F/B control with a lean air-fuel ratio (e.g., A/F=23) as a target air-fuel ratio.

The detailed description will be made hereinbelow. In the flowchart of FIG. 5, the ECU 26 first calculates a basic injection amount Tp at step 100. The basic injection amount Tp is calculated in accordance with the engine speed NE and intake pressure PM at that time by using, for example, an injection amount map, pre-stored in the ROM. Further, the ECU 26 determines at the next step 110 whether or not feedback control condition (feedback condition) is satisfied. As it is well known, the feedback condition is satisfied when the cooling water temperature Thw is predetermined value or greater and the engine does not drive at a high speed and with high load.

If the feedback condition is satisfied, the ECU 26 proceeds to step 120, and determines by the throttle opening TH, for example, whether or not the vehicle is in acceleration condition. At this time, if the determination at the step 120 is affirmative, the ECU 26 proceeds to step 130, and sets the target air-fuel ratio λTG to the stoichiometric target value (A/F=14.7) so as to perform feedback control at the stoichiometric ratio (logical air-fuel ratio). On the other hand, if the determination at step 120 is negative, the ECU 26 proceeds to lath step 140, and sets the target air-fuel ratio λTG to the lean target value (e.g., A/F=about 23) so as to perform feedback control at the lean region. The determination to perform the stoichiometric F/B control or the lean F/B control may be performed by using the engine speed or intake pressure information so as to perform the lean burn control when the vehicle is in stable running condition.

Thereafter, the ECU 26 reads the air-fuel ratio l (A/F value) from the bias controller 40 at step 150, and at the next step 160, sets a feedback correction coefficient FAF so as to use the air-fuel ratio λ as the target air-fuel ratio λTG. The feedback correction coefficient FAF is calculated by using the following equations (1) and (2). The setting of the feedback correction coefficient FAF is disclosed in Japanese Patent Application Laid-Open No. 1-110853.

[Expression 1]

$$FAF(k) = K1 \cdot \lambda(k) - \sum_{n=1}^{k} Kn+1 \cdot FAFn + ZI(k) \tag{1}$$

$$ZI(k)=ZI(k-1)+Ka \cdot (\lambda(k)-\lambda TG) \tag{2}$$

In the above equations (1) and (2), k represents a variable indicative of the number of control times from the start of sampling; K1 to Kn+1, an appropriate feedback gain; ZI(k), an integral term; and ka, an integral constant.

Further, if the feedback condition is not satisfied at step 110, the ECU 26 proceeds to step 170, and sets the feedback correction coefficient FAF to "1.0" so as to perform the air-fuel ratio open control. After the calculation of the feedback correction coefficient FAF, the ECU 26 calculates a fuel injection amount TAU by using the following equation (3).

$$TAU=Tp \cdot FAF \cdot FALL \tag{3}$$

That is, the fuel injection amount TAU is set from the basic injection amount Tp, the feedback correction coefficient FAF and other correction coefficients FALL (various correction coefficients for the engine water temperature, electric load and the like), thereafter, the ECU 26 ends the present routine.

Next, voltage control upon air-fuel ratio (limit-current value) detection by the A/F sensor 30 will be described. The present embodiment has the following main features:

At each of plural times of air-fuel ratio (sensor current value) detection, a target voltage value is set by using one of applied-voltage characteristic lines having different change rates of the applied-voltage.

At each of plural times of air-fuel ratio (sensor current value) detection, the applied-voltage change speed is variably set sequentially.

The outline of these features will be described with reference to a V-I characteristic diagram of FIG. 8.

According to the V-I characteristic diagram of FIG. 8, in respective (1)–(4) regions to be described below, the air-fuel ratio is detected with high precision by the A/F sensor 30. That is, in the present embodiment, the regions where the air-fuel ratio is detected with high precision are:

(1) a stoichiometric ratio peripheral region where the target air-fuel ratio is set for stoichiometric F/B control. The air-fuel ratio is, for example, 13 to 17 (in FIG. 8, region C where sensor current=−6 to 5 mA), (2) a lean burn region where the target air-fuel ratio is set for lean burn F/B control. The air-fuel ratio is, for example, 20 to 26 (in FIG. 8, region E where sensor current=10 to 16 mA), (3) an atmosphere detection region (in FIG. 8, region G where sensor current>27 mA) accompanying fuel cut-off, (4) a predetermined rich region where the air-fuel ratio is less than 12 (in FIG. 8, region A where sensor current<−11 mA).

Figure 27:
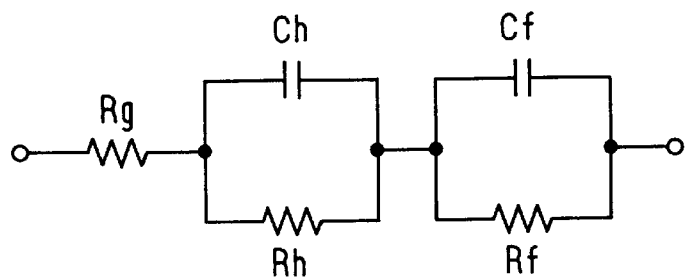
FIG. 27 is a diagram showing the equivalent electric circuit of the A/F sensor.

In these regions, an applied-voltage characteristic line L1 for setting a voltage applied to the A/F sensor 30 is substantially upright, which means that the applied-voltage is fixed in the above regions (1) to (4). In this case, even if the air-fuel ratio varies in the above regions (1) to (4), the applied-voltage is not varied, and the sensor current does not inadvertently vary due to the influence of current change by condenser characteristic (the equivalent circuit in FIG. 27) of the zirconia sensing element.

In regions other than the above regions (1) to (4), i.e., regions where sensor current=−11 to −6 mA, 5 to 10 mA, and 16 to 27 mA (regions B, D and F in FIG. 8), the air-fuel ratio is not detected with high precision. For this reason, the applied-voltage characteristic line L1 has a slope, and the applied-voltage is variably set in accordance with the air-fuel ratio at different times.

The above region (4) is necessary in a case where the fuel injection amount is incrementally feedback-controlled at high-load driving time or low-temperature starting time, for example. This control ensures drivability at high-load driving time or low-temperature starting time, and realizes reduced emission. In the present embodiment, the content of the control will be omitted.

On the other hand, as described above, in the present embodiment, the applied-voltage change speed is variably set in accordance with an air-fuel ratio detection region. This setting will be described with reference to FIG. 8.

(a) In regions where sensor current=less than −11 mA, −6 to 5 mA, 10 to 16 mA, and 27 mA or greater (in FIG. 8, the regions A, C, E and G), the applied-voltage is varied with a reference speed "5 mV/4 ms".

(b) In regions where sensor current=−11 to −6 mA, and 5 to 10 mA (in FIG. 8, the regions B and D), the applied-voltage is varied with a speed "5 mV/8 ms" slower than the reference speed.

(c) In a region where sensor current=16 to 27 mA (in FIG. 8, the region F), the applied-voltage is varied with a speed "10 mV/4 ms" faster than the reference speed.

The reason why the applied-voltage change speed is varied with the region (a) as a reference is as follows. That is, in the above regions (b), air-fuel ratio information is obtained with high-precision detection while the influence by the above-described condenser characteristic of the A/F sensor 30 is avoided, and for this purpose, the applied-voltage is varied slowly. Further, in the above region (c), the air-fuel ratio detection is unnecessary, and the applied-voltage change speed is made faster with priority to air-fuel ratio detection so as to follow the abrupt change of the air-fuel ratio upon fuel cut-off.

Figure 9:
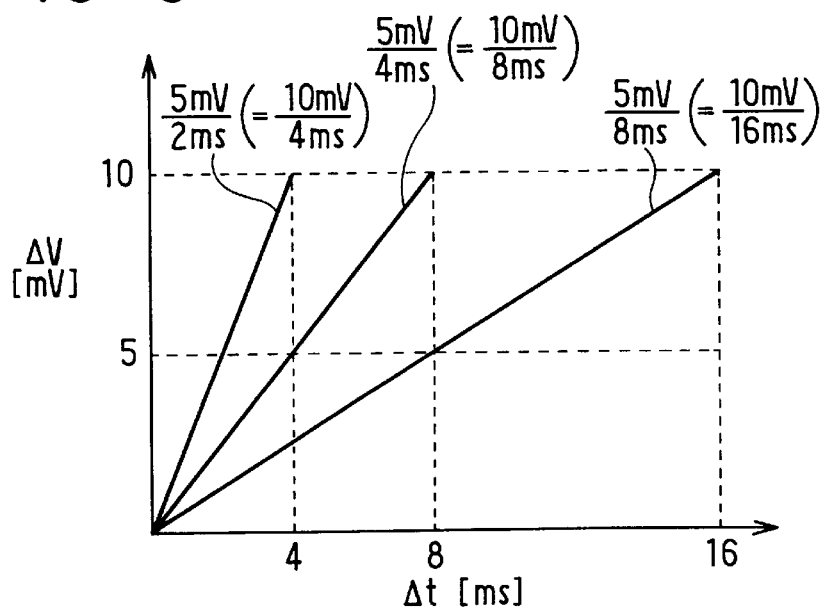
FIG. 9 is a graph showing applied-voltage change speeds used in the first embodiment.

In this case, three types of speeds as shown in FIG. 9 are employed as the applied-voltage change speed. FIG. 9 shows the relation of voltage change amount $\Delta V$ per unit time $\Delta t$. In FIG. 9, 5 mv/4 ms (=10 mV/8 ms) represents a reference change speed; 5 mV/8 ms (=10 mV/16 ms), a change speed slower than the reference change speed; and 5 mV/2 ms (=10 mV/4ms) represents a change speed faster than the reference change speed.

Figure 6:
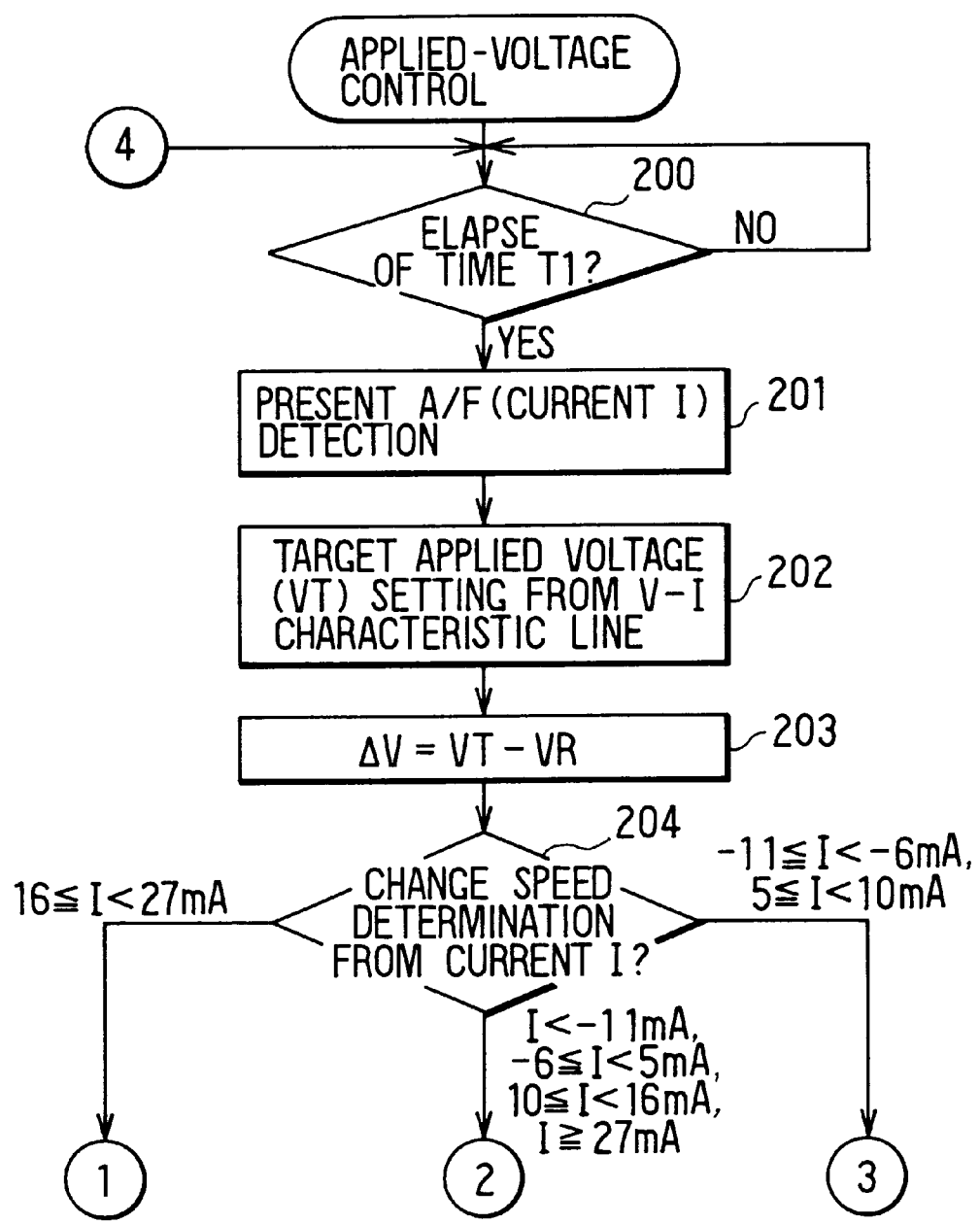
FIG. 6 is a flowchart showing an applied-voltage control routine in the first embodiment.
Figure 7:
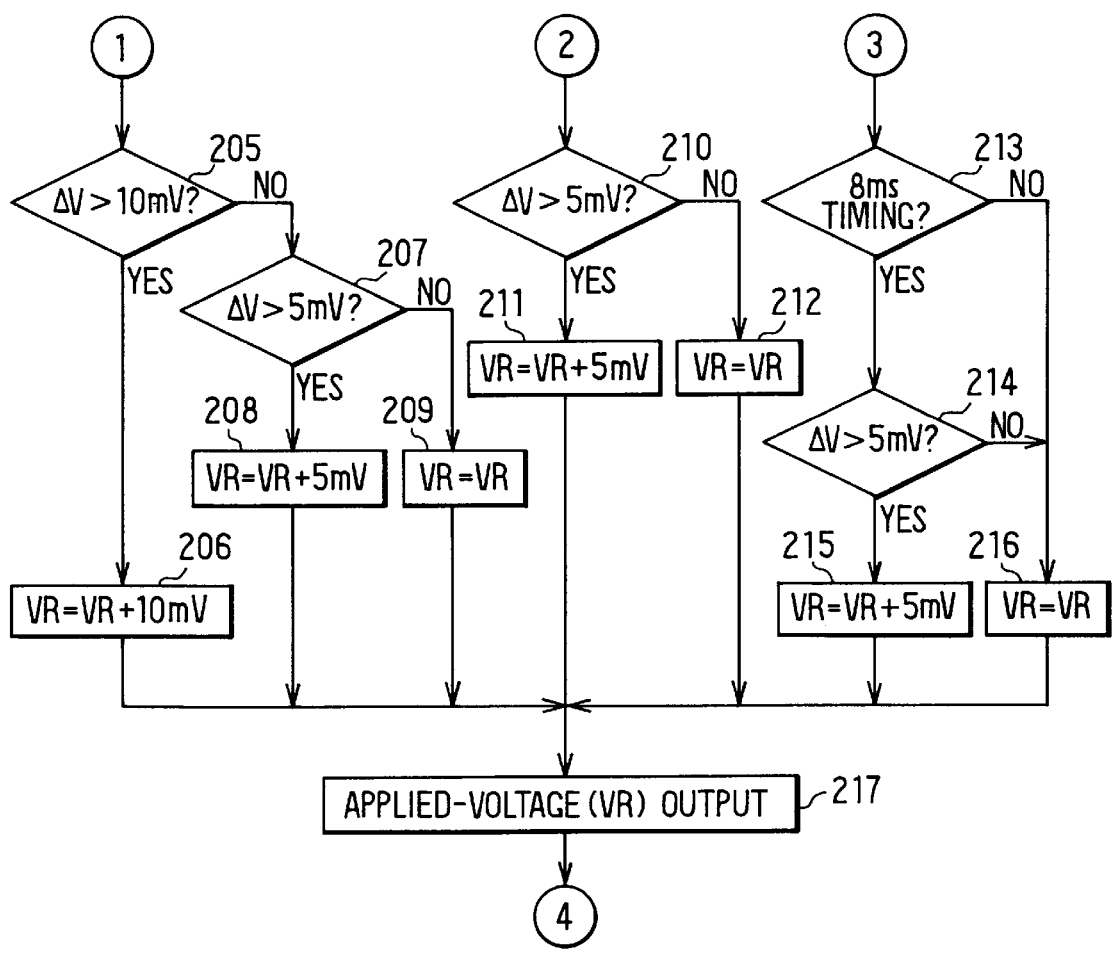
FIG. 7 is a flowchart showing an applied-voltage control routine which follows from that of FIG. 6.

Hereinbelow, a procedure of applied-voltage control upon air-fuel ratio detection by the A/F sensor 30 will be described with reference to a flowchart of FIGS. 6 and 7. The flowcharts of FIGS. 6 and 7 is started by the microcomputer 20 when the power is turned on.

First, the microcomputer 20 determines at step 200 whether or not a predetermined period T1 has elapsed from previous sensor current detection. The predetermined period T1 corresponds to a detection period of sensor current value I, and appropriately set to T1=about 2 to 4 ms (millisecond), for example. If the predetermined period T1 has elapsed from the previous sensor current detection, the microcomputer 20 determines at step 200 affirmatively, then proceeds to step 201. At step 201, the microcomputer 20 reads the sensor current value (limit-current value) I detected by the current detector 50. At this time, an air-fuel ratio of the engine corresponding to the sensor current value I at that time may be detected by using the characteristic map pre-stored in the ROM of the microcomputer 20.

Thereafter, at step 202, the microcomputer 20 determines a target applied-voltage value VT to be applied to the A/F sensor 30, based on the sensor current value at that time. In this case, the applied-voltage characteristic line L1 as shown in the V-I characteristic diagram of FIG. 8 is used. That is, as described above, in the regions requiring high air-fuel detection precision (the stoichiometric control region, the lean burn control region, the atmosphere detection region and the rich control region), the target applied-voltage value VT is set as a fixed value, on the other hand, in a regions other than the above regions not requiring such high detection precision, the target applied-voltage value VT is variably set.

Further, at step 203, the microcomputer 20 subtracts a voltage value VR currently applied to the A/F sensor 30 from the target voltage value VT, as the change amount $\Delta V$ of the applied-voltage ($\Delta V=VT-VR$). The change amount $\Delta V$ corresponds to the deviation of the applied-voltage.

Thereafter, the microcomputer 20 determines setting condition of the applied-voltage change speed in accordance with the sensor current value I, at step 204. At this time, the change speed of 5 mV/4 ms is used as a reference change speed; the speed of 10 mV/4 ms, as a change speed faster than the reference change speed; and the speed of 5 mV/8 ms, as a change speed slower than the reference change speed. Accordingly, if the sensor current value I is any of I<−11 mA, −6<I<5 mA, 10<I<16 mA, and I>27 mA (in any of the regions A, C, E and G in FIG. 8), the microcomputer 20 proceeds to step 210 in FIG. 7, and sets the change speed such that the applied-voltage varies at the reference change speed at steps 210 to 212. Further, if the sensor current value I is 16<I<27 mA (in the region F in FIG. 8), the microcomputer 20 proceeds to step 205 in FIG. 7, and sets the change speed such that the applied-voltage varies at the change speed faster than the reference change speed at steps 205 to 209. Further, if the sensor current value I is any of −11<I<−6 mA, 5<I<10 mA (in any of the regions B and D in FIG. 8), the microcomputer 20 proceeds to step 213 in FIG. 7, and sets the change speed such that the applied-voltage varies at the change speed slower than the reference change speed at steps 213 to 216.

If the applied-voltage is varied at the reference change speed (5 mV/4 ms), the microcomputer 20 determines at step 210 in FIG. 7 whether or not the change amount $\Delta V$ of the applied-voltage exceeds 5 mV. In this case, if $\Delta V>5$ mV holds, the microcomputer 20 proceeds to step 211, adds 5 mV to the present value VR of the applied-voltage, and if $\Delta V<5$ mV holds, holds the present value VR of the applied-voltage without any change. After the applied-voltage setting, the microcomputer 20 proceeds to step 217, outputs the above value VR as the applied-voltage value, and returns to step 200 in FIG. 6. By this operation, a desired voltage is applied to the A/F sensor 30 via the D/A converter 21 and the bias controller 40.

The present embodiment employs the D/A converter 21 having a resolution of 5 mV/LSB. If the change amount DV of the applied-voltage is lower than the resolution, the applied-voltage is not changed. However, it may be arranged such that, in a case where the change amount $\Delta V$ of the applied-voltage is less than 5 mV, if rounding the $\Delta V$ value results in 5 mV, the applied-voltage is changed.

Further, in the case where the applied-voltage is varied at the change speed faster than the reference change speed (10 mV/4 ms), the microcomputer 20 determines at step 205 in FIG. 7 whether or not the change amount $\Delta V$ of the applied-voltage exceeds 10 mV. In this case, if $\Delta V>10$ mV holds, the microcomputer 20 proceeds to step 211, and adds 10 mV to the applied-voltage present value VR. That is, as the deviation of the applied-voltage is large, the applied-voltage is changed at one time (at a high speed). On the other hand, if $\Delta V<10$ mV holds at step 205, the microcomputer 20 proceeds to step 207, then determines whether or not the change amount of the applied-voltage exceeds 5 mV, and if $\Delta V>5$ mV holds, holds the present applied-voltage value VR without any change. After the voltage setting, the microcomputer 20 proceeds to step 217, and outputs the above value VR as the applied-voltage value.

Further, when the applied-voltage is varied at the change speed (5 mV/8 ms) slower than the reference change speed, as the present processing is performed at 4 ms intervals, the applied-voltage is updated at most once per two times. Then, the microcomputer 20 determines at step 213 in FIG. 7 whether or not the current time is at 8 ms timing, i.e., it is time to vary the applied-voltage. If the determination at step 213 is affirmative, the microcomputer 20 proceeds to step 214, and determines whether or not the calculated change amount ΔV of the applied-voltage exceeds 5 mV. In this case, if the determinations at steps 213 and 214 are both affirmative, the microcomputer 20 proceeds to step 215, and adds 5 mV to the present applied-voltage value VR. On the other hand, if any of the determinations at steps 213 and 214 is negative, the microcomputer 20 proceeds to step 216, and holds the present applied-voltage value VR without any change. After the applied-voltage setting, the microcomputer 20 proceeds to step 217, and outputs the above value VR as the applied-voltage value.

Further, although the detailed description will be omitted in the present specification, the air-fuel ratio control apparatus according to the present embodiment detects the air-fuel ratio of atmosphere by the A/F sensor 30 in a fuel cut-off condition, and detects abnormality or degradation condition of the A/F sensor 30 from the result of detection. That is, if the A/F sensor 30 is in normal condition, when the air-fuel ratio greatly moves toward the lean side upon fuel cut-off, a high sensor current is obtained. In this case, as the sensor current value upon atmosphere detection is already known, abnormality of the sensor is easily detected based on the result of detection of the air-fuel ratio (sensor current) upon fuel cut-off. Further, the difference among individual sensor characteristics is obtained.

According to the present embodiment as described in detail above, the following effects are obtained.

(a) In the present embodiment, in the stoichiometric control region (the region C in FIG. 8), the lean burn control region (the region E in FIG. 8), the atmosphere detection region (the region G in FIG. 8) and the rich control region (the region A in FIG. 8), the change rate of the voltage applied to the A/F sensor 30 is reduced to be less than that in other regions. Specifically, the applied-voltage characteristic line L1 is made vertical to the axis V, and in the above regions, the applied-voltage has a fixed value.

Figure 28:
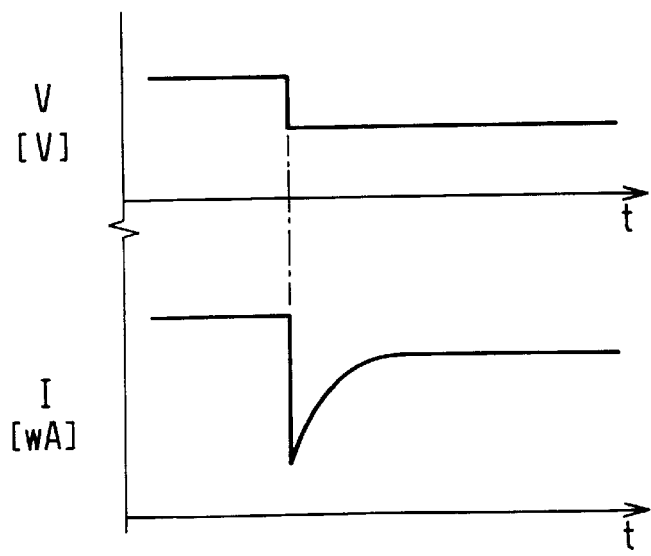
FIG. 28 is a time chart showing the problems encountered in the conventional apparatus.

In this case, the voltage is applied to the A/F sensor 30 in a state where the influence of the capacitive (condenser) characteristic of the A/F sensor 30 is avoided. Accordingly, this prevents the problem that the sensor current generates a peak current immediately after the voltage change from the influence of electric charge accumulated in the condenser, whereby time required until until the peak current converges into a predetermined current value is prolonged, as in the conventional apparatuses (FIG. 28). Further, since the air-fuel ratio can be detected with high precision in a ultra-rich region or ultra-lean region by using the voltage having a fixed value as described above, the air-fuel ratio detection range can be widened. As a result, it is possible to improve the air-fuel ratio detection precision while widely detecting the air-fuel ratio.

(b) In this case, in a region where the change rate of the applied-voltage is reduced, the voltage applied to the A/F sensor 30 has a fixed value, therefore, the construction can be simplified to attain the object of the present invention.

(c) As described above, since the air-fuel ratio can be detected with high precision in the stoichiometric control region and the lean burn control region, the result of detection can be more efficiently reflected to air-fuel ratio feedback control. That is, high-precision air-fuel ratio feedback control can be performed upon execution of the stoichiometric control together with the lean burn control, which removes inconvenience such as emission degradation.

(d) Further, since the air-fuel ratio (sensor current value) can be detected with high precision in the atmosphere detection region, degradation condition of the A/F sensor 30 can be determined with high precision by comparing the sensor current value detected upon atmosphere detection accompanying fuel cut-off with the already-known sensor current value upon the atmosphere detection. Further, the result of detection of the sensor current value upon atmosphere detection can be used for correcting the difference of the individual sensor characteristics.

(e) In addition, in the present embodiment, when the voltage applied to the A/F sensor 30 is changed, the applied-voltage change speed is variably set sequentially. Specifically, three types of change speed are provided for each sensor current value (air-fuel ratio). In this construction, as described above, a voltage is applied to the sensor without influence of the condenser characteristic of the A/F sensor 30, which removes the conventional problem due to the condenser characteristic. In this case, as appropriate detection processing can be performed in all the air-fuel ratio detection regions, the region where the air-fuel ratio can be detected with high precision can be widened.

(f) Further, in the present embodiment, when the change rate of applied-voltage is varied, the voltage width is varied (Steps 205 to 209 in FIG. 7), and the time period is varied (steps 213 to 216 in FIG. 7). This is one method to vary the applied-voltage change speed, and according to this method, the applied-voltage change speed can be easily varied.

Figure 8:
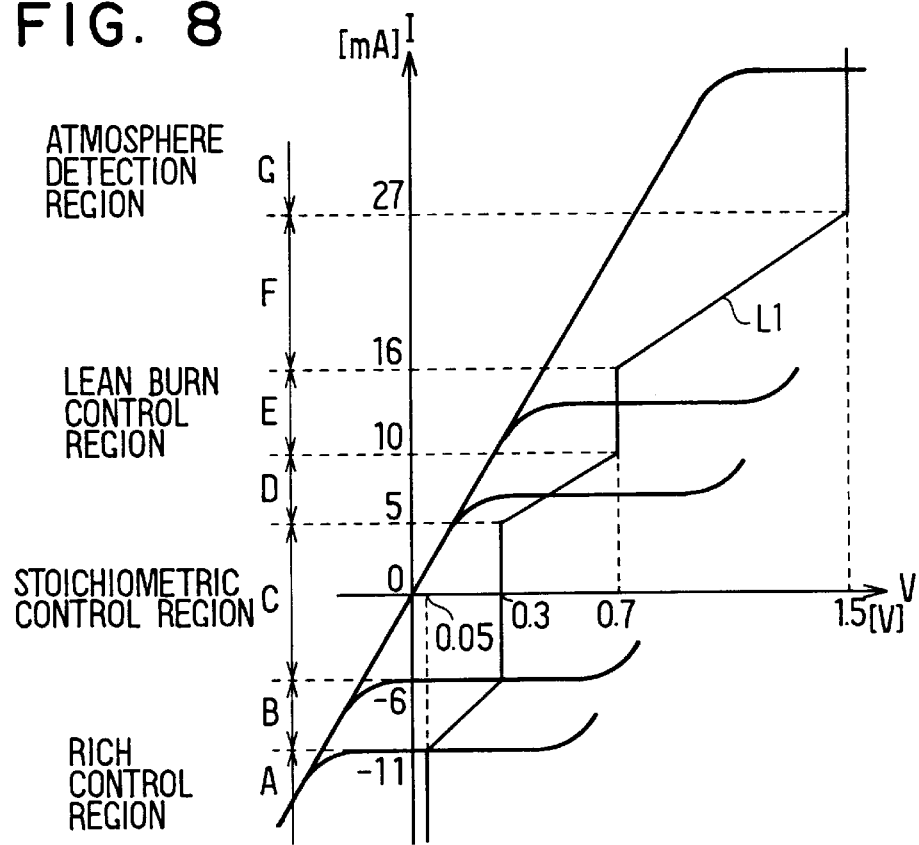
FIG. 8 is a V-I characteristic diagram for explaining an applied-voltage characteristic line used in the first embodiment.

(g) Further, in the present embodiment, when atmosphere detection processing is performed in the middle of air-fuel ratio control, the applied-voltage change speed is increased to be faster than the previous change speed (the region F in FIG. 8). That is, upon atmosphere detection performed with fuel cut-off, for example, the air-fuel ratio varies abruptly. Generally, the air-fuel ratio is not detected in the middle of abrupt change of the air-fuel ratio, therefore, the applied-voltage change speed is increased to improve the response characteristics of air-fuel ratio detection with priority.

(h) Further, in regions where a target air-fuel ratio is set (the stoichiometric control region "C" in FIG. 8 and the lean burn control region "E" in FIG. 8), the change rate of the voltage applied to the A/F sensor 30 is reduced to be less than that in other regions, and in regions adjacent to the regions where the change rate is reduced (the regions B and D in FIG. 8), the applied-voltage change speed is reduced to be slower than the reference change speed (5 mV/4 ms). In this case, in the regions where the target air-fuel ratio is set, the change rate of the applied-voltage is reduced, so that the air-fuel ratio detection precision in the regions is improved, as described above. On the other hand, if the applied-voltage change speed in regions adjacent to the regions where the target air-fuel ratio is set is reduced to be slower than that in other regions, the air-fuel ratio detection precision which is transitional around the boundary of the regions where the target air-fuel ratio is set (around sensor current value=−6 mA, 5 mA, and 10 mA) can also be improved.

In the above embodiment, the target applied-voltage value VT is set based on the V-I characteristic diagram of FIG. 8. Especially in a region requiring high air-fuel ratio detection precision, the applied-voltage has a fixed value. In addition, the applied-voltage change speed is variably set sequentially. However, if the above embodiment is modified for the purpose of simplification of the construction, the object of the present invention can be attained.

Figure 10:
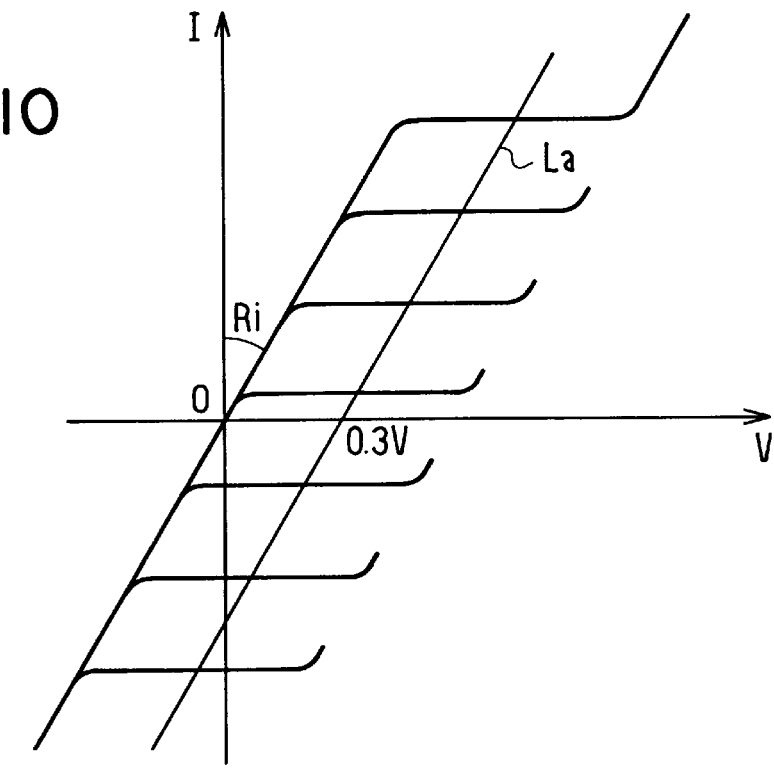
FIG. 10 is a V-I characteristic diagram showing a linear applied-voltage characteristic line used in the modification of the first embodiment.

That is, for example, the region where the applied-voltage has a fixed value (a segment vertical to the axis V in FIG. 8) is deleted, and as shown in FIG. 10, a characteristic line La corresponding to an internal-resistance Ri of the A/F sensor 30 is set. In this case, as the applied-voltage varies with the same slope in any region, the applied-voltage varies even in a region requiring high air-fuel ratio detection precision. However, as described with reference to the routine in FIGS. 6 and 7, if the applied-voltage change speed is variably set at times, the air-fuel ratio detection precision is improved in a desired region, thus, the object of the present invention is attained. Further, this construction has advantage that it is unnecessary to pre-store a complicated map (applied-voltage characteristic lines) into the memory.

Further, it may be arranged such that the target applied-voltage value VT is set based on the applied-voltage characteristic line L1 in the above FIG. 8 (the applied-voltage in a region requiring high air-fuel ratio detection precision has a fixed value), while the applied-voltage change speed is fixed to a constant value. Specifically, in the routine of FIGS. 6 and 7, the processing at steps 203 to 216 is deleted. In this case, in comparison with the above embodiment, the detection precision is slightly degraded, however, the air-fuel ratio detection precision is improved in a desired region. Thus, it is apparent that the object of the present invention is attained.

Next, second to fifth embodiments of the present invention will be described. In the following respective embodiments, the explanation of a part similar to that of the above first embodiment will be generally made, and hereinafter, the differences from the first embodiment will be mainly described.

(Second Embodiment)

Hereinbelow, the second embodiment of the present invention will be described with reference to FIGS. 11 and 12. The present embodiment has a purpose to limit sensor current which flows in a region outside a pre-set air-fuel ratio detection range (FIG. 3), within a predetermined range. The outline of the present embodiment will be described with reference to a V-I characteristic diagram of FIG. 11.

Figure 11:
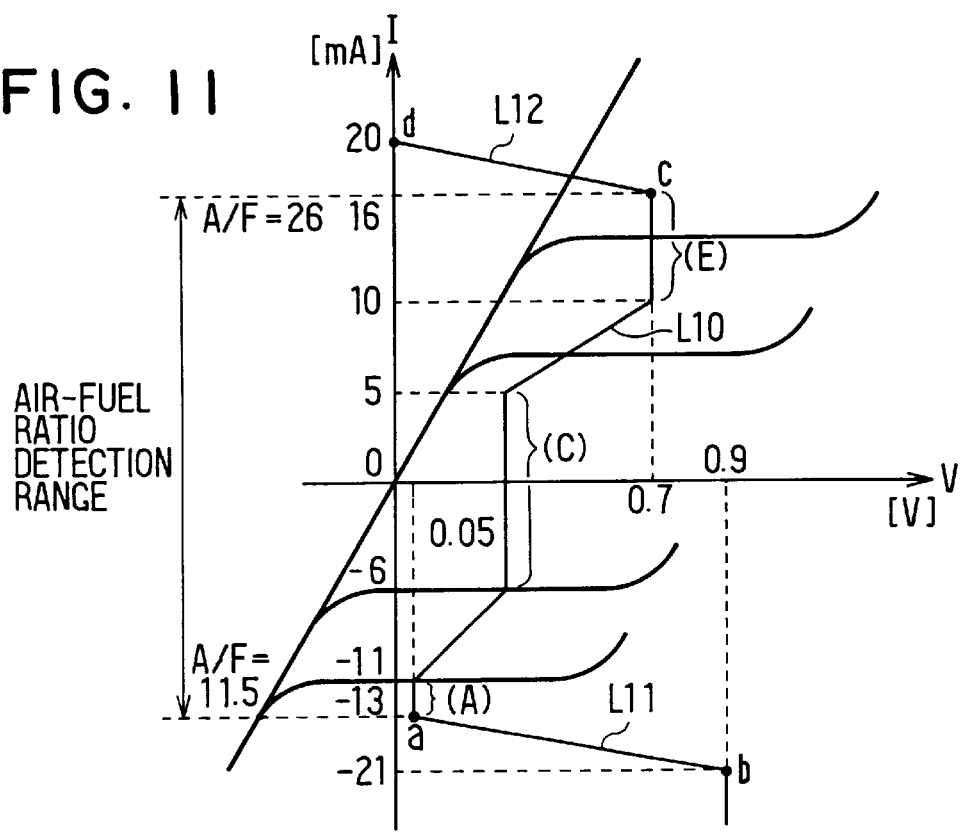
FIG. 11 is a V-I characteristic diagram showing the applied-voltage characteristic line to limit the current value within a predetermined range according to the second embodiment.
Figure 12:
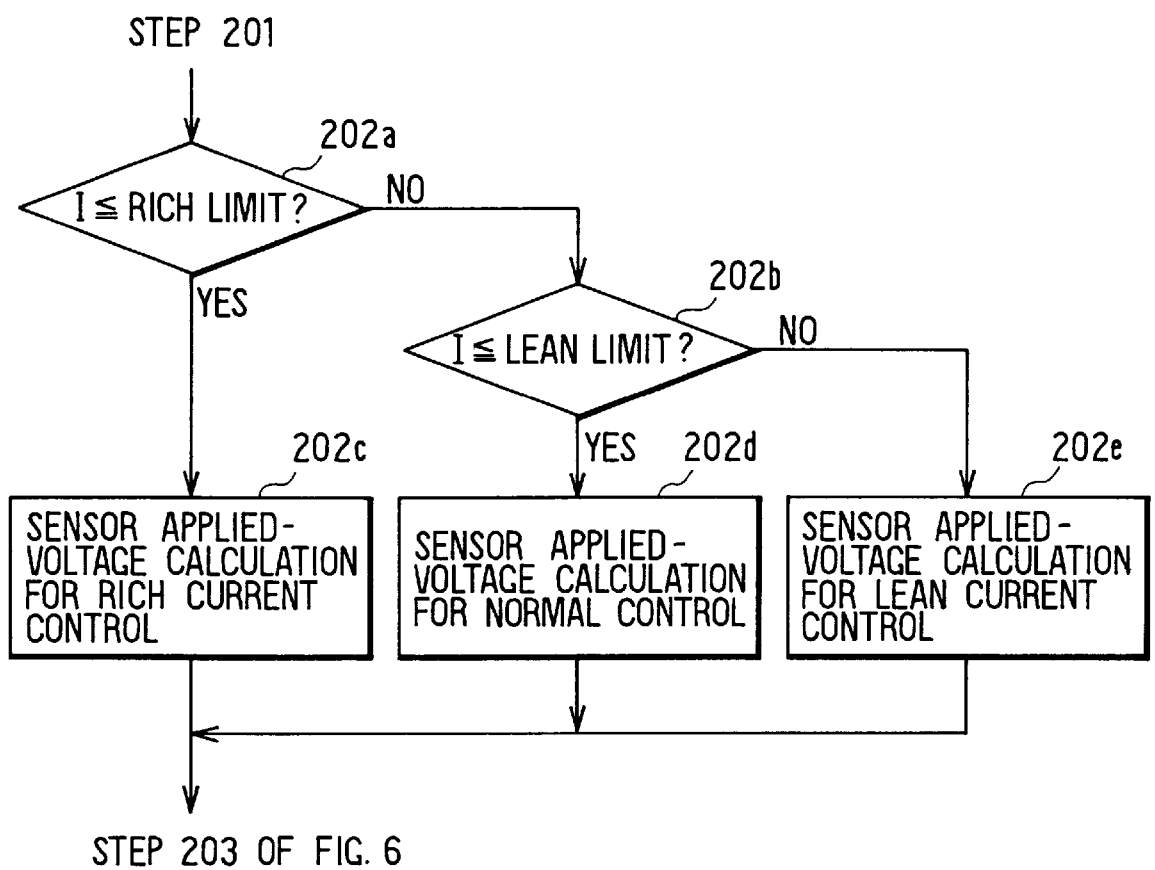
FIG. 12 is a flowchart showing a part of the applied-voltage control routine in the second embodiment.

In FIG. 11, a range of A/F=11.5 to 26 (range of sensor current=−13 to 16 mA) is the "air-fuel ratio detection range". In this range, a characteristic line L10 similar to the characteristic line L1 in the first embodiment is set, and an applied-voltage is controlled by using the characteristic line L10. The characteristic line L10 has a stoichiometric control region (A/F=13 to 17), a lean burn control region (A/F=20 to 26) and a rich control region (A/F=11.5 to 12), however, lacks an atmosphere detection region outside the air-fuel ratio detection region. The characteristic line L10 has a portion where the applied-voltage has a fixed value in the respective three regions, however, as a whole, the characteristic line L10 has a positive characteristic (positive slope) that, as one of the voltage or current increases, the other increases.

Then, on the rich side from the air-fuel ratio detection range (A/F<11.5), a characteristic line L11 having a negative slope (a slope opposite to that of the characteristic line L10) is set. At this time, in FIG. 11, at a point a, the above characteristic line L10 has the rich limit of the air-fuel ratio detection range, and at a point b, there is an intersection between the rich-side limit of a predetermined sensor current detection range (not shown) and a rich-side electromotive force (0.9 V) of the A/F sensor 30. Further, the characteristic line L11 has a one-dimensional straight-line segment connecting the points a and b. The further rich side from the point b of the characteristic line L11 is a linear segment (always 0.9 V) parallel to an axis I.

Further, on the lean side from the air-fuel ratio detection range (A/F>26), a characteristic line L12 having a negative slope (a slope opposite to that of the characteristic line L10) is set. At this time, in FIG. 11, at a point c, the characteristic line L10 has the lean limit of the air-fuel ratio detection range, and at a point d, there is an intersection between the lean limit of a predetermined sensor current detection range (not shown) and a lean-side electromotive force (0 V) of the A/F sensor 30. Further, the characteristic line L12 has a one-dimensional straight-line segment connecting the points c and d. The further lean side from the point d of the characteristic line L12 is a straight line segment (always 0 V) parallel to the axis I.

By setting the characteristic lines L11 and L12 as described above, in the state as shown in FIG. 11, in the region outside the air-fuel ratio detection range, the sensor current which flows at that time is naturally limited within a predetermined range (e.g., the pre-set sensor current detection range in circuit design).

Hereinbelow, a procedure of executing the applied-voltage control according to the present embodiment will be described with reference to a flowchart of FIG. 12. The flowchart of FIG. 12 shows additional processing to the processing at step 202 in FIG. 6 in the first embodiment, and other processings in the applied-voltage control routine in FIGS. 6 and 7 are as described above. In the processing in FIG. 12, the vale of a voltage applied to the A/F sensor 30 is determined based on the characteristic lines L10, L11 and L12.

Specifically, the microcomputer 20 determines at step 202a whether or not a sensor current value I is the rich limit of the air-fuel ratio detection range or less, i.e., whether or not the current value corresponds to A/F=11.5 or less. If the sensor current value I is the rich limit of the air-fuel ratio detection range or less, the microcomputer 20 determines affirmatively at step 202a and proceeds to step 202c, while if the sensor current value I is greater than the rich limit of the air-fuel ratio detection range, proceeds to step 202b.

Further, the microcomputer 20 determines at step 202b whether or not the sensor current value I is the lean limit of the air-fuel ratio detection range or less, i.e., whether or not the sensor current value corresponds to A/F=26 or less. If the sensor current value I is the lean limit of the air-fuel ratio detection range or less, the microcomputer 20 determines affirmatively at step 202b and proceeds to step 202d, while if the sensor current value I is greater than the lean limit of the air-fuel ratio detection range, proceeds to step 202e.

In a case where the microcomputer 20 proceeds to step 202c (in case of I<rich limit), the microcomputer 20 calculates a target applied-voltage value VT (a voltage applied to the sensor for rich current control) corresponding to the sensor current value I detected by the previous processing, by using the characteristic line L11 in FIG. 11. Further, in a case where the microcomputer 20 proceeds to step 202d (in case of rich limit<I<lean limit), the microcomputer 20 calculates a target applied-voltage value VT (a voltage value for normal control) corresponding to the sensor current value I, by using the characteristic line L10 in FIG. 11. Further, in a case where the microcomputer 20 proceeds to step 202e (in case of I>lean limit), the microcomputer 20 calculates a target applied-voltage value VT (a voltage applied to the sensor for lean current control) corresponding to the sensor current value I, by using the characteristic line L12 in FIG. 11. Processings other than the above processing in FIG. 12 such as the setting of applied-voltage change speed are similar to those described above, therefore, the explanation of those processings will be omitted.

According to the present embodiment, similar to the above-described first embodiment, the object of the present invention is attained, and the following additional effects are obtained.

(a) In the present embodiment, in a region outside the air-fuel ratio detection range (A/F<11.5 and A/F>26 in FIG. 11), the voltage applied to the A/F sensor 30 is controlled so as to limit the sensor current to a predetermined value. Specifically, in the air-fuel ratio detection range, the applied-voltage is controlled with a predetermined positive characteristic on the V-I coordinates (characteristic line L10 in FIG. 11), while in a region outside the air-fuel ratio detection range, the applied-voltage is controlled with a characteristic different from the positive characteristic (characteristic lines L11 and L12 in FIG. 11).

That is, in a region outside the air-fuel ratio detection range, monotonous applied-voltage control corresponding to the air-fuel ratio may cause a problem in that a large amount of current flows through the A/F sensor 30, and the like. In the present embodiment, the problem where an excessive amount of current flows through the A/F sensor 30 and the like can be avoided by limiting the sensor current. As a result, in the region outside the air-fuel ratio detection range, the sensor current can be appropriately suppressed, and precise current detection can be performed. In addition, the heat-generating amount of the bias controller 40 (specifically, heat-generating amount by driving the transistor in the bias controller) for application of a voltage to the A/F sensor 30 can be greatly reduced.

(b) Especially, in a case where the sensor current is on the rich side from the air-fuel ratio detection range, the characteristic line L11 in FIG. 11 is used to gradually control the applied-voltage so as to approach the maximum electromotive force (0.9 volt) of the A/F sensor 30. In a case where the sensor current is on the lean side from the air-fuel ratio detection range, the characteristic line L12 is used to control the applied-voltage so as to approach the minimum value (0 volt) of the A/F sensor 30. This construction limits the sensor current within a predetermined range and prevents current flow exceeding this range. Even when the sensing element internal-resistance of the A/F sensor 30 varies and the slope of the resistance dominant region varies, the sensor current can be suppressed within a predetermined range regardless of these changes.

(c) Further, according to the present embodiment, even when the air-fuel ratio greatly approaches to the lean or rich side, the sensor current value is always detected within a predetermined sensor current detection range, therefore, the internal-resistance can be detected whenever it is necessary to detect the sensing element internal-resistance of the A/F sensor 30 from the applied-voltage and the sensor current value.

The above sensor current control processing may be constructed as follows, as well as the above construction. For example, in a region outside the air-fuel ratio detection range, the applied-voltage is feedback controlled such that the sensor current value (air-fuel ratio) becomes a predetermined value. In this case, as the sensor current value is controlled to the target value, the sensor current does not increase nor decreases abruptly. Accordingly, similar to the above embodiment, the sensor current can be appropriately detected in a region outside the air-fuel ratio detection range. Further, the heat-generating amount of the bias controller 40 can be greatly suppressed.

(Third Embodiment)

Next, the third embodiment of the present invention will be described with reference to FIGS. 13 to 16. In the above embodiments, as the air-fuel ratio feedback control apparatus, a system which executes stoichiometric F/B control and lean burn F/B control is constructed, and the outline of the system has been described. In the present embodiment, a system which executes only the stoichiometric F/B control will be described. Further, in the present embodiment, the sensing element internal-resistance Ri of the A/F sensor 30 is detected in accordance with necessity, and a plurality of characteristic lines for setting an applied-voltage in correspondence with the sensing element internal-resistance Ri are selectively used.

Figure 13:
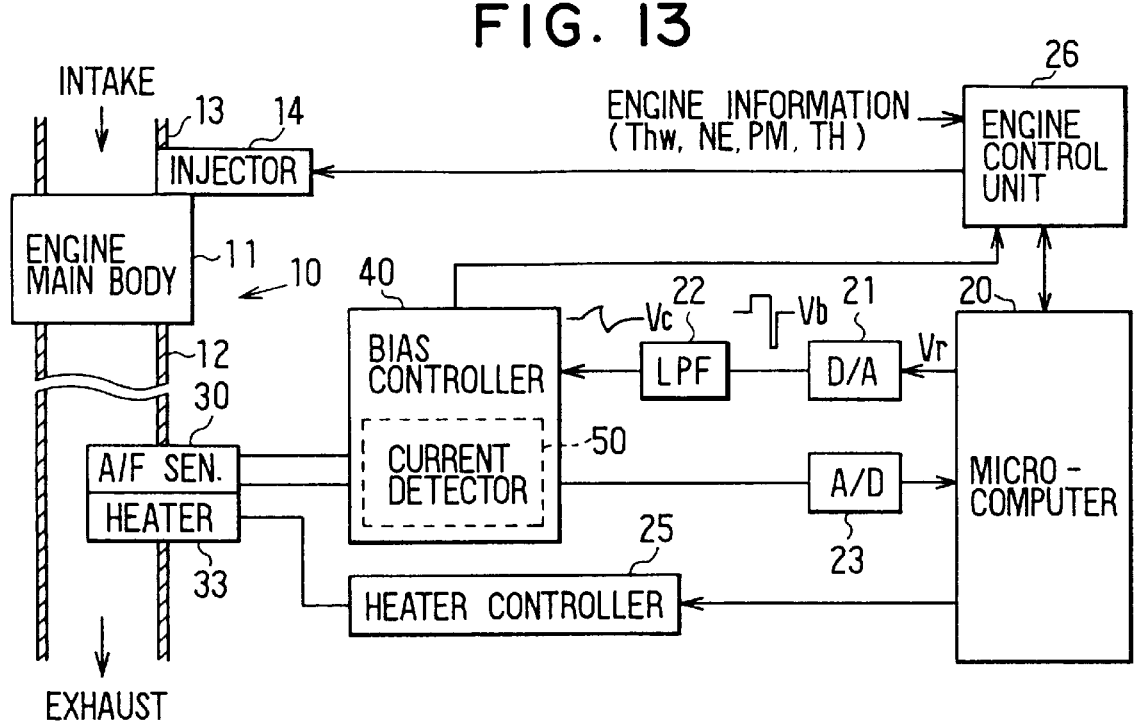
FIG. 13 is a block diagram showing the schematic construction of the air-fuel ratio feedback control apparatus according to the third embodiment.

FIG. 13 is a block diagram showing the schematic construction of the air-fuel ratio control apparatus of the present embodiment.

FIG. 13 shows a modification to a part of FIG. 1 in the above first embodiment. In FIG. 13, an LPF (low pass filter) 22 is provided on the output side of the D/A converter 21 which inputs the bias command signal Vr from the microcomputer 20. Accordingly, a high-frequency component in the analog signal Vb outputted from the D/A converter 21 is removed by the LPF 22, and the signal becomes an output voltage Vc. This voltage Vc is inputted into the bias controller 40 as an air-fuel ratio detection voltage or detection voltage of sensing element internal-resistance. At this time, upon air-fuel ratio detection, an applied-voltage corresponding to the air-fuel ratio (sensor current value) at that time is set by the applied-voltage characteristic line in the V-I characteristic diagram, on the other hand, upon sensing element internal-resistance detection, a voltage of a predetermined frequency signal, with a one-shot and predetermined time constant, is applied.

Next, the operation of the air-fuel ratio control apparatus having the above construction will be described.

In the present embodiment, as described above, as the air-fuel ratio feedback control, only stoichiometric F/B control, without lean burn F/B control, is executed. For this purpose, the present embodiment uses FIG. 16 as the V-I characteristic diagram, and sets an applied-voltage based on an applied-voltage characteristic line L21 in FIG. 16 (represented with a solid line). The applied-voltage characteristic line L21 in FIG. 16 has three regions as high-precision air-fuel ratio detection regions:

(1) a stoichiometric ratio peripheral region where a target air-fuel ratio is set by the stoichiometric F/B control; the air-fuel ratio is, e.g., 13 to 17 (a region where sensor current=−6 to 5 mA holds)

(2) an atmosphere detection region (a region where sensor current>27 mA holds) following a fuel cut-off (3) a predetermined rich region where the air-fuel ratio is, e.g., less than 12 (a region where sensor current<−11 mA holds).

That is, in the above three regions, the applied-voltage characteristic line L21 is vertical to the axis V such that the applied-voltage has a fixed value.

Figure 16:
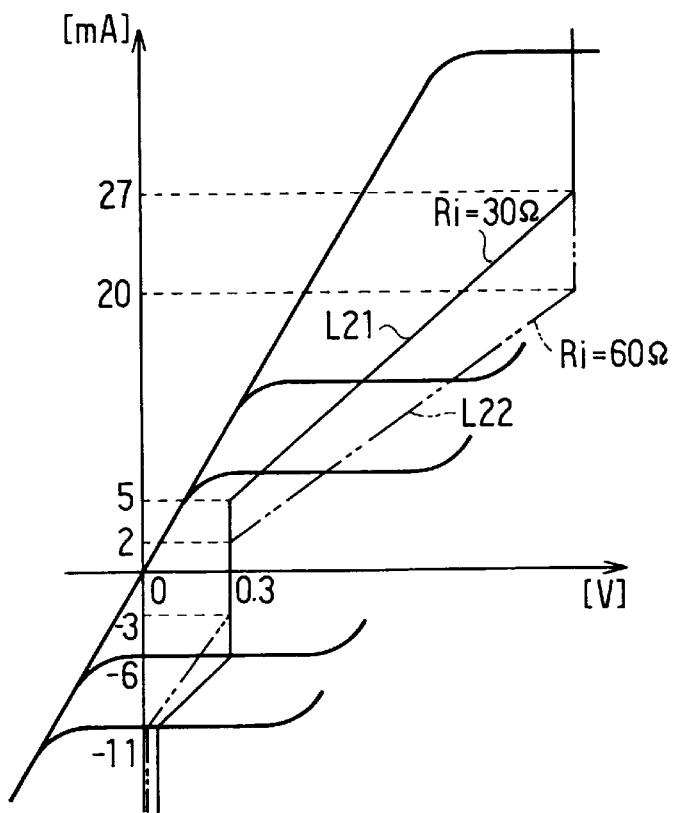
FIG. 16 is a V-I characteristic diagram showing the applied-voltage characteristic line in the third embodiment.

In FIG. 16, the characteristic line L21 represented with the solid line is an applied-voltage characteristic line when the internal-resistance Ri is 30 Ω, while a characteristic line L22 represented with a two-dot dashed line is an applied-voltage characteristic line when the internal-resistance Ri is 60 Ω. Thus, in practice, it is desirable to change the characteristic line in accordance with the internal-resistance Ri which can be a parameter of active condition of the A/F sensor 30, for example, and the change of the characteristic line is similarly desirable in the V-I characteristic diagram of FIG. 8 in the above-described first embodiment (in FIG. 8, the applied-voltage characteristic line can be set by each Ri with a substantially similar tendency).

Figure 14:
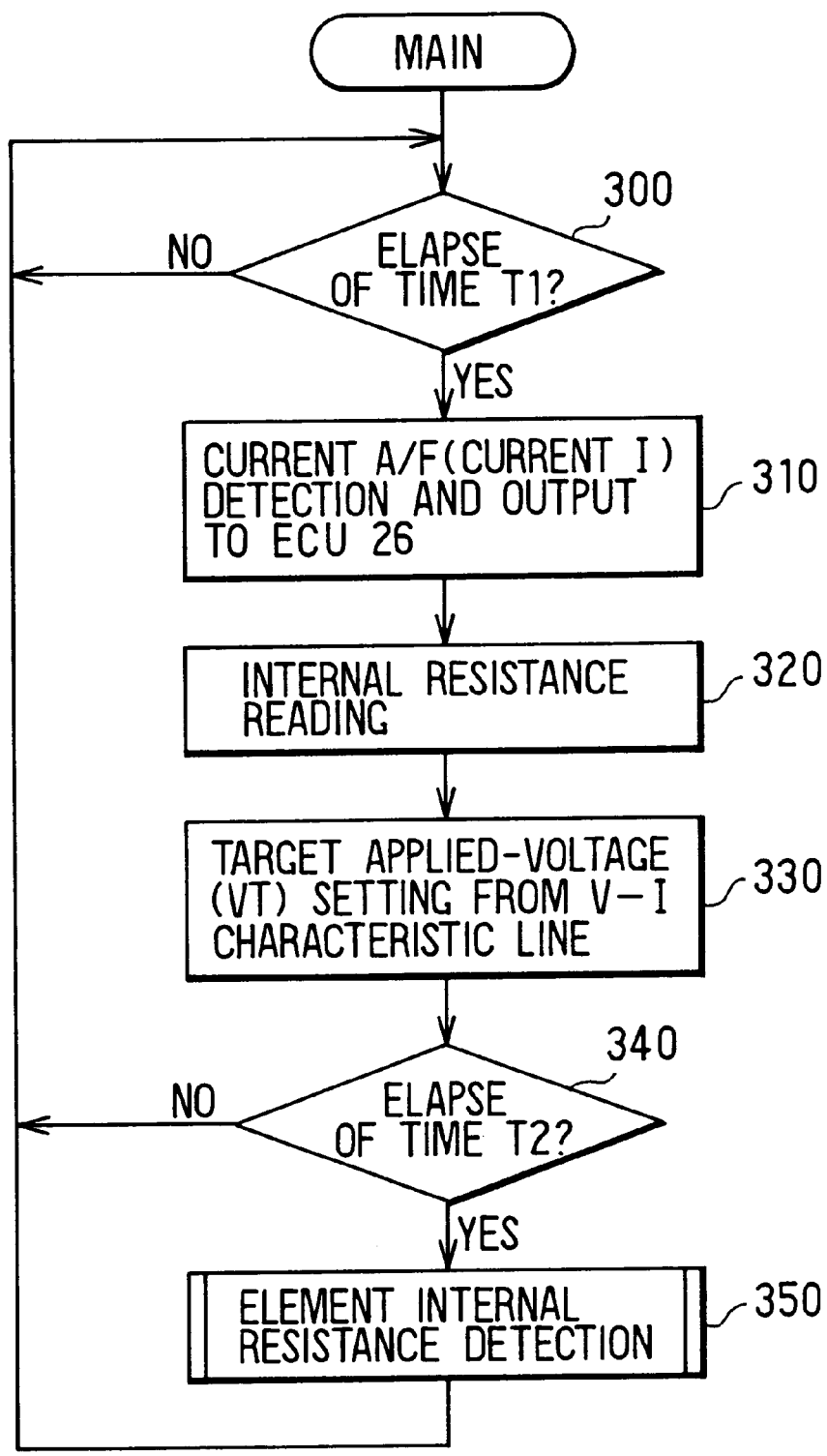
FIG. 14 is a flowchart showing the main routine of the microcomputer in the third embodiment.

FIG. 14 is a flowchart showing a main routine of the microcomputer 20 according to the present embodiment. In FIG. 14, the microcomputer 20 first determines at step 300 whether or not a predetermined period T1 has elapsed since the previous air-fuel ratio detection. The predetermined period T1 corresponds to the period of air-fuel ratio detection. The period T1 is set to, e.g., T1=about 2 to 4 ms. If the predetermined period T1 has elapsed since the previous air-fuel ratio detection, the microcomputer 20 determines affirmatively at step 300 and proceeds to step 310. The microcomputer 20 reads the sensor current value I (limit-current value) detected by the current detector 50 at step 310, and outputs the detection result to the engine control unit ECU 26.

Thereafter, at step 320, the microcomputer 20 reads the internal-resistance Ri (RAM value) of the A/F sensor 30 calculated in accordance with a procedure to be described later. Then, the microcomputer 20 sets the target applied-voltage value VT corresponding to the read sensor current value I and the internal-resistance Ri, while referring to the characteristic line L21 (or the characteristic line L22) in the V-I characteristic diagram of FIG. 16, at step 330.

Further, the microcomputer 20 determines at step 340 whether or not a predetermined period T2 has elapsed from the previous internal-resistance detection. The predetermined period T2 corresponds to the period of internal-resistance detection. The period T2 is selectively set in accordance with, e.g., engine driving condition. In the present embodiment, when the change in the air-fuel ratio is relatively small (in normal engine driving), the period is set to T2=2 s (second), while when the air-fuel ratio abruptly varies (in transitional engine driving), the period is set to T2=128 ms (millisecond). If the determination at step 340 is negative, the microcomputer 20 detects the air-fuel ratio (sensor current value) each time the predetermined period T1 has elapsed. If the determination at step 340 is affirmative, the microcomputer 20 detects the sensing element internal-resistance at step 350. The internal-resistance detection processing will be described with reference to a subroutine of FIG. 15.

Figure 15:
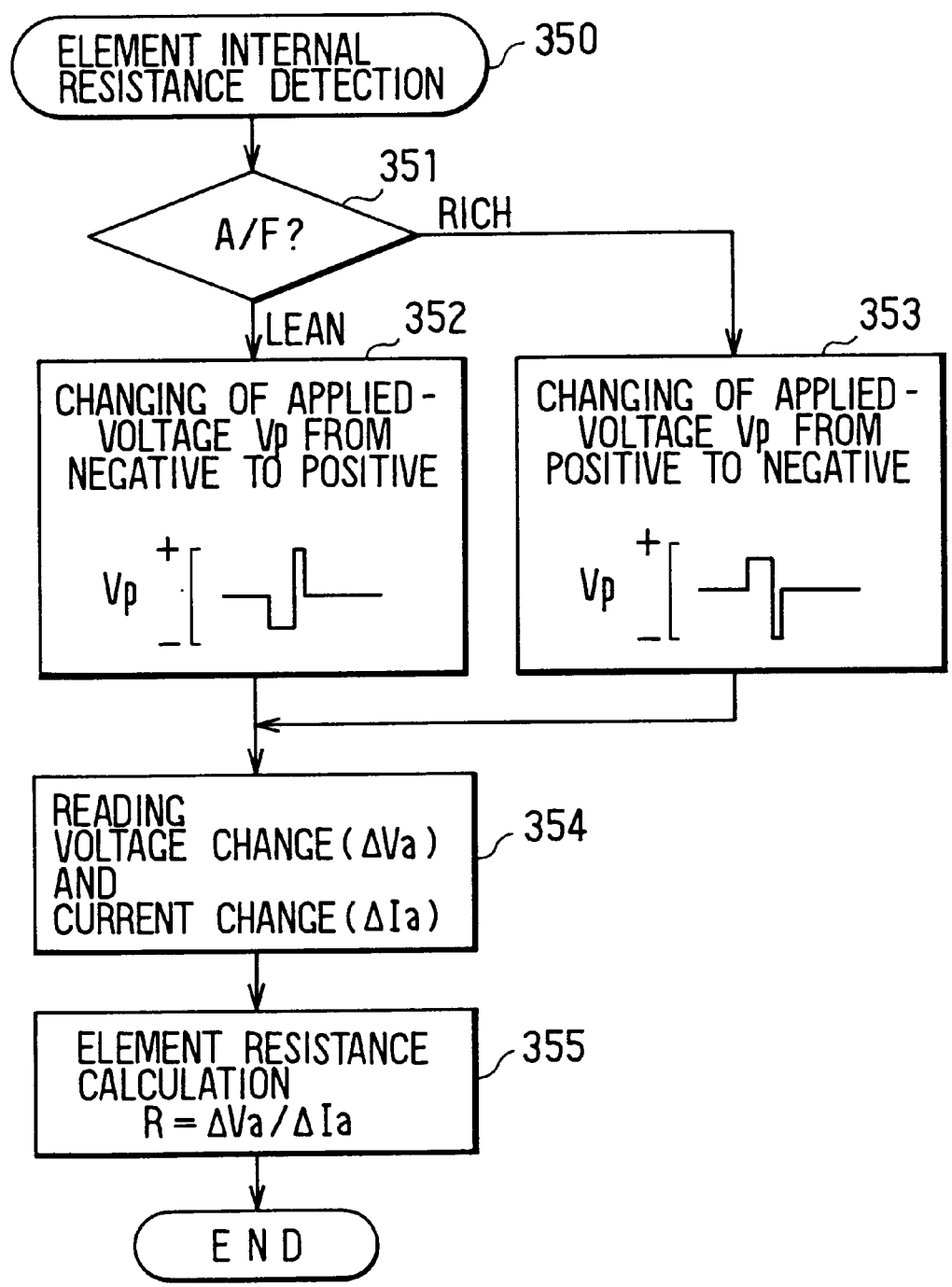
FIG. 15 is a flowchart showing the sensing element internal-resistance detection subroutine in the third embodiment.

In FIG. 15, the microcomputer 20 first determines at step 351 whether or not the current air-fuel ratio is rich or lean. If air-fuel ratio=lean holds, the microcomputer 20 varies the applied-voltage Vp (A/F detection voltage) by that time from the negative side→the positive side, at step 352, while if air-fuel ratio=rich holds, varies the applied-voltage Vp from the positive side→the negative side (operates the bias command signal Vr), at step 353.

Then, after the applied-voltage change, the microcomputer 20 reads a voltage change amount $\Delta Va$ and a sensor-current change amount DIa detected by the current detector 50, at step 354. Thereafter, the microcomputer 20 calculates the internal-resistance Ri by using the change amounts $\Delta Va$ and $\Delta Ia$ (Ri=$\Delta Va/\Delta Ia$), at step 355, then returns to the main routine. The calculated value Ri is utilized for feedback control on the electric power for the heater 33. This feedback control maintains the active condition of the A/F sensor 30.

As described above, the present embodiment attains the object of the present invention, similar to the above embodiment, further, obtains the following additional effects.

(a) The present embodiment variably sets a region where the change rate of the applied-voltage is reduced in accordance with the sensing element internal-resistance of the A/F sensor 30 (the V-I characteristic diagram of FIG. 16). Accordingly, air-fuel ratio detection with higher precision can be realized.

(b) Further, the present embodiment changes the voltage applied to the A/F sensor 30 to detect an air-fuel ratio to the voltage to detect the sensing element internal-resistance with a predetermined time constant, and detects the sensing element internal-resistance from the voltage change and the current change following the voltage change. That is, according to this construction, upon changing the applied-voltage to the voltage to detect the sensing element internal-resistance, abrupt occurrence of current peak can be suppressed. As a result, a precise sensor current value can be measured, and further, the sensing element internal-resistance of the A/F sensor 30 can be detected with high precision. Thus, as the sensing element internal-resistance is precisely detected, the precision of air-fuel ratio detection can be improved.

(c) The present embodiment uses the LPF 22 to apply an alternating current signal having a predetermined time constant to the A/F sensor 30. Accordingly, the embodiment obtains advantageous effects such as high-precision detection of sensing element internal-resistance with simpler construction. In this case, as the microcomputer 20 only generates a square-wave digital signal, high-load operation processing is not required. Therefore, an air-fuel ratio detecting apparatus with high reliability can be provided.

(Fourth Embodiment)

The fourth embodiment shows a modification to the above third embodiment. As described in the V-I characteristic diagram of FIG. 11, this embodiment has a purpose to limit sensor current which flows upon detection, in a region outside a pre-set air-fuel ratio detection range, within a predetermined range. The outline of this embodiment will be described with reference to a V-I characteristic diagram of FIG. 17.

Figure 17:
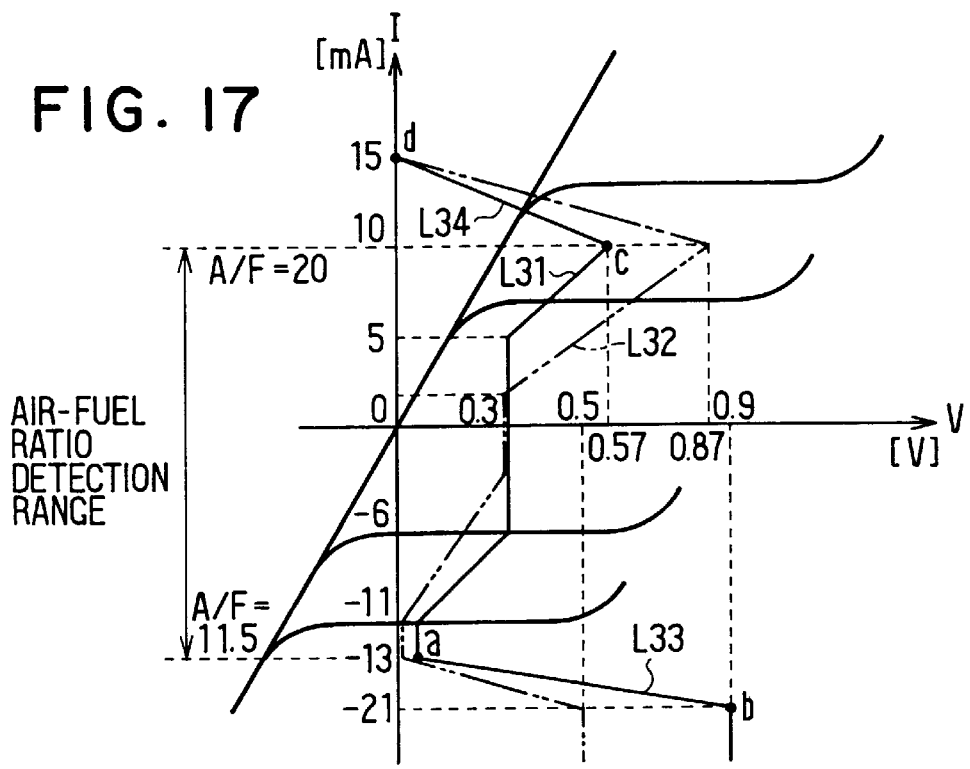
FIG. 17 is a V-I characteristic diagram showing the applied-voltage characteristic line in the fourth embodiment.

That is, according to FIG. 17, a range of A/F=11.5 to 20 (sensor current value=–13 to 10 mA) is the "air-fuel ratio detection range". In this range, characteristic lines L31 and L32 similar to the characteristic lines L21 and L22 in the third embodiment are set, and the applied-voltage is controlled by using the characteristic lines L31 and L32. The characteristic line L31 indicates a characteristic where internal-resistance Ri=30 $\Omega$, and the characteristic line L32, a characteristic where internal-resistance Ri=60 $\Omega$. Hereinbelow, description will be made mainly using the characteristic line L31. That is, the characteristic line L31 has a stoichiometric control region (A/F=13 to 17) where the applied-voltage has a fixed value and a rich control region (A/F=11.5 to 12), but lacks an atmosphere detection region outside the air-fuel ratio detection range. Further, the characteristic line L31 has portions where the applied-voltage has a fixed voltage respectively in the two regions, however, has, as a whole, a positive characteristic (positive slope) where as one of the voltage and current increases, the other one of them increases.

On the rich side (A/F<11.5) from the air-fuel ratio detection range, a characteristic line L33 having a negative slope (a slope opposite to that of the characteristic line L31) is set. At this time, at a point a, the characteristic line L31 has a rich limit of the air-fuel ratio detection range, and at a point b, there is an intersection between a rich-side limit of a predetermined sensor-current detection range and a rich-side electromotive force (0.9 V) of the A/F sensor 30. The characteristic line L33 has a one-dimensional straight-line segment connecting the points a and b. The far-rich side from the point b of the characteristic line L33 is a linear segment parallel to the axis I (always 0.9 V).

Further, on the lean side (A/F>20) from the air-fuel ratio detection range, a characteristic line L34 having a negative slope (a slope opposite to that of the characteristic line L31) is set. At this time, at a point c, the characteristic line L31 has a lean limit of the air-fuel ratio detection range, and at a point d, there is an intersection between a lean-side limit of a predetermined sensor-current detection range and a lean-side electromotive force (0 V) of the A/F sensor 30. The characteristic line L34 has a one-dimensional straight-line segment connecting the points c and d. The far-lean side from the point d of the characteristic line L34 is a straight line segment parallel to the axis I (always 0 V).

As described above, by setting the characteristic lines L33 and L34 as described above, in the state as shown in FIG. 17, in a region outside the air-fuel ratio detection range, the sensor current which flows at that time is naturally limited within a predetermined range (e.g., within a sensor current detection range pre-set in circuit designing).

According to the present embodiment, similar to the above-described respective embodiments, the object of the present invention is attained, and further, additional effects as follows are obtained. That is, the present embodiment controls a voltage applied to the A/F sensor 30 such that in a region outside the air-fuel ratio detection range (regions where A/F<11.5 and A/F>20 in FIG. 11), the sensor current is limited to a predetermined value. Accordingly, the problem that excessive sensor current flows, or the like, can be avoided, and appropriate current detection can be performed. In addition, the heat-generating amount of the bias controller 40 to apply a voltage to the A/F sensor 30 can be greatly reduced.

(Fifth Embodiment)

Next, the fifth embodiment of the present invention will be described with reference to FIG. 18. This embodiment discloses a method other than described above regarding the procedure of setting the applied-voltage change speed. Specifically, the embodiment sets the applied-voltage change speed in accordance with the change amount $\Delta V$ as the difference between the target applied-voltage value VT and the actual applied value VR at times.

Figure 18:
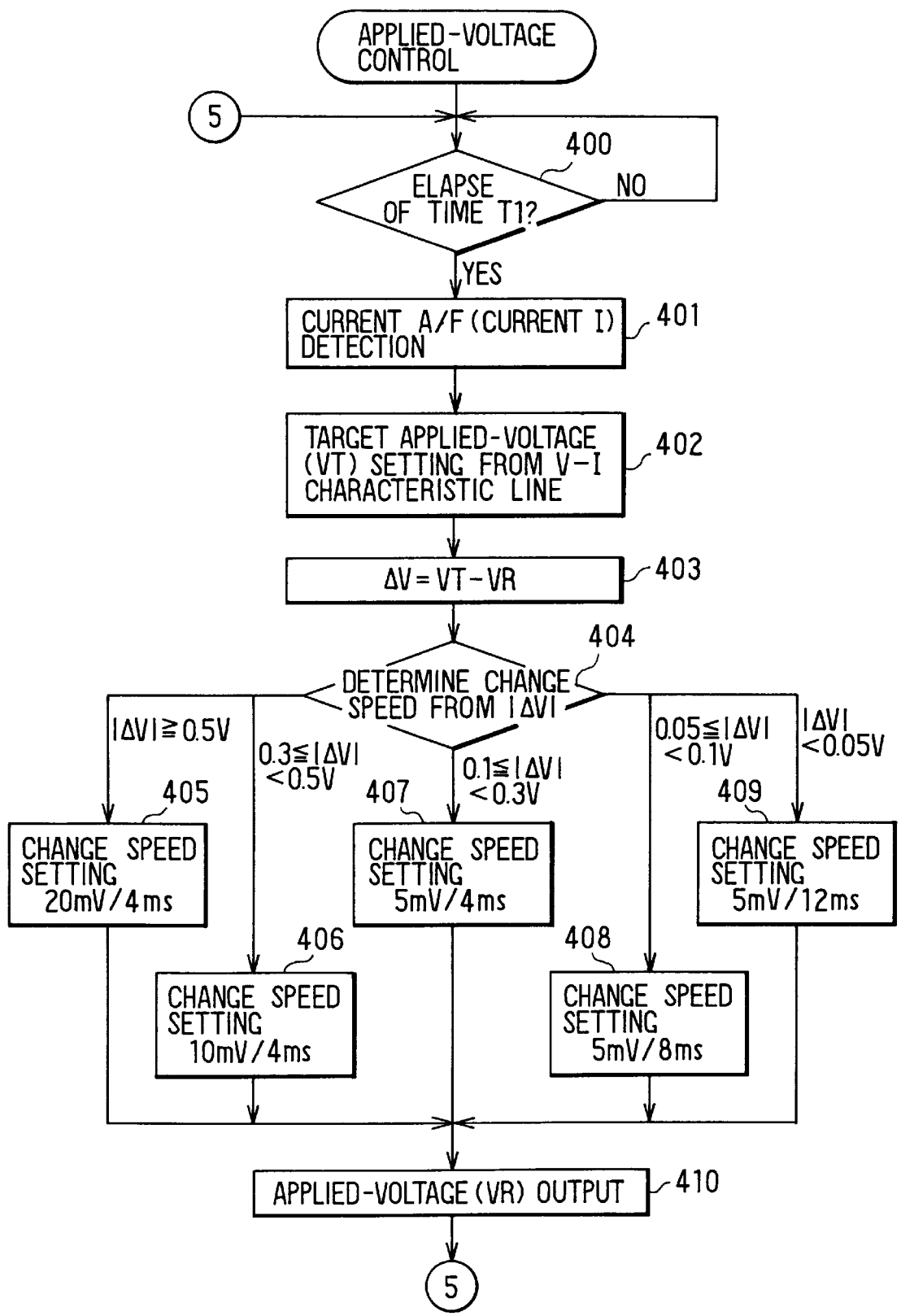
FIG. 18 is a flowchart showing the applied-voltage control routine according to the fifth embodiment.

FIG. 18 is a flowchart showing an applied-voltage control routine. The flowchart is started when the power of the microcomputer 20 is turned on. Hereinafter, the flowchart of FIG. 18 will be described in due order.

When the flowchart of FIG. 18 starts, the microcomputer 20 first determines at step 400 whether or not the predetermined period T1 (e.g., about 2 to 4 ms) has elapsed since previous sensor current detection. If the predetermined period T1 has elapsed since the previous sensor current detection, the microcomputer 20 determines at step 400 affirmatively and proceeds to step 401. The microcomputer 20 reads the sensor current value (limit-current value) I detected by the current detector 50 at step 401. At this time, it may be possible to detect the air-fuel ratio of the engine corresponding to the sensor current value I at that time by using the characteristic map pre-stored in the ROM of the microcomputer 20.

Thereafter, the microcomputer 20 determines the target applied-voltage value VT to be applied to the A/F sensor 30 based on the sensor current value at that time, at step 402. In this case, the applied-voltage characteristic line L1 described in the V-I characteristic diagram of FIG. 8 is used. That is, as described above, in regions requiring high air-fuel ratio detection precision (a stoichiometric control region, a lean burn control region, an atmosphere detection region and a rich control region), the target applied-voltage value VT is set as a fixed value, while in regions not requiring such high air-fuel ratio detection precision, the target applied-voltage value VT is variably set.

When setting the target applied-voltage value VT, a characteristic diagram without a lean burn control region such as shown in the above FIG. 16 may be used. In this case, in the stoichiometric control region, the atmosphere detection region and the rich region as regions requiring high air-fuel ratio detection precision, the target applied-voltage value VT is set as a fixed value, while in regions not requiring such high air-fuel ratio detection precision, the target applied-voltage value VT is variably set. Further, in a region outside the air-fuel ratio detection range, when the sensor current which flows at that time is limited within a predetermined range, the target applied-voltage value VT is set by using the V-I characteristic diagram such as the above-described FIG. 11 or FIG. 17. Further, as shown in the above-described FIG. 10, the target applied-voltage value VT may be set by using a characteristic line La of a linear segment (a characteristic line without a fixed voltage portion).

Further, the microcomputer 20 subtracts the voltage value VR currently applied to the A/F sensor 30 from the target applied-voltage value VT set at step 403, as the change amount $\Delta V$ of the applied-voltage ($\Delta V = VT - VR$). The change amount $\Delta V$ corresponds to the deviation of the applied-voltage.

Thereafter, the microcomputer 20 determines the conditions for setting the applied-voltage change speed in accordance with the absolute value of the voltage change amount $\Delta V$, at step 404. At this time, with a change speed of 5 mV/4 ms as a reference speed, a speed of 20 mV/4 ms and a speed of 10 mv/4 ms are set as change speeds faster than the reference change speed, and a speed of 5 mv/8 ms and a speed of 5 mV/12 ms as change speeds slower than the reference change speed to the greater value. The microcomputer 20 sets the applied-voltage change speed to a greater value as the voltage change amount $\Delta V$ increases, while the microcomputer 20 sets the applied-voltage change speed to a less value as the voltage change amount $\Delta V$ decreases. Specifically, if $|\Delta V| > 0.5$ V holds, the microcomputer sets the change speed such that the applied-voltage varies at the change speed "20 mV/4 ms" at step 405;

if $0.3 \text{ V} < |\Delta V| < 0.5$ V holds, the microcomputer sets the change speed such that the applied-voltage varies at the change speed "10 mV/4 ms" at step 406;

if $0.1 \text{ V} < |\Delta V| < 0.3$ V holds, the microcomputer sets the change speed such that the applied-voltage varies at the change speed "5 mV/4 ms" at step 407;

if $0.05 \text{ V} < |\Delta V| < 0.1$ V holds, the microcomputer sets the change speed such that the applied-voltage varies at the change speed "5 mV/8 ms" at step 408; and if $|\Delta V| < 0.05$ V holds, the microcomputer sets the change speed such that the applied-voltage varies at the change speed "5 mV/12 ms" at step 409.

Then, when the applied-voltage change speed is determined as above, the microcomputer 20 outputs the applied-voltage VR (varies the voltage value) in accordance with the above change speeds such that the voltage value becomes the determined target value VT at step 410. Thereafter, the microcomputer 20 returns to step 400 to repetitively perform similar processing.

In the applied-voltage changing processing (steps 405 to 409), if the resolution of the D/A converter 21 is 5 mV/LSB, basically the voltage value cannot be changed if the voltage change amount $\Delta V$ is less than 5 mV (however, in a case where the amount becomes 5 mV by rounding, the voltage change may be possible). On the other hand, if the change speed is faster than the reference speed (5 mV/4 ms), the voltage width is changed at one time in correspondence with the resolution of the D/A converter 21. This processing corresponds to steps 205 to 209 in the above-described FIG. 7. Further, if the change speed is slower than the reference speed (5 mV/4 ms), the applied-voltage is varied at one time per plural times. This processing corresponds to steps 213 to 216 in FIG. 7.

According to the present embodiment, similar to the respective embodiments, the object of the present invention can be attained. Especially, as the present embodiment sets the applied-voltage change speed in accordance with the applied-voltage change amount ΔV, appropriate processing can be performed with the value ΔV as a parameter.

The embodiments of the present invention are not limited to the above embodiments but can be embodied as follows.

Figure 19:
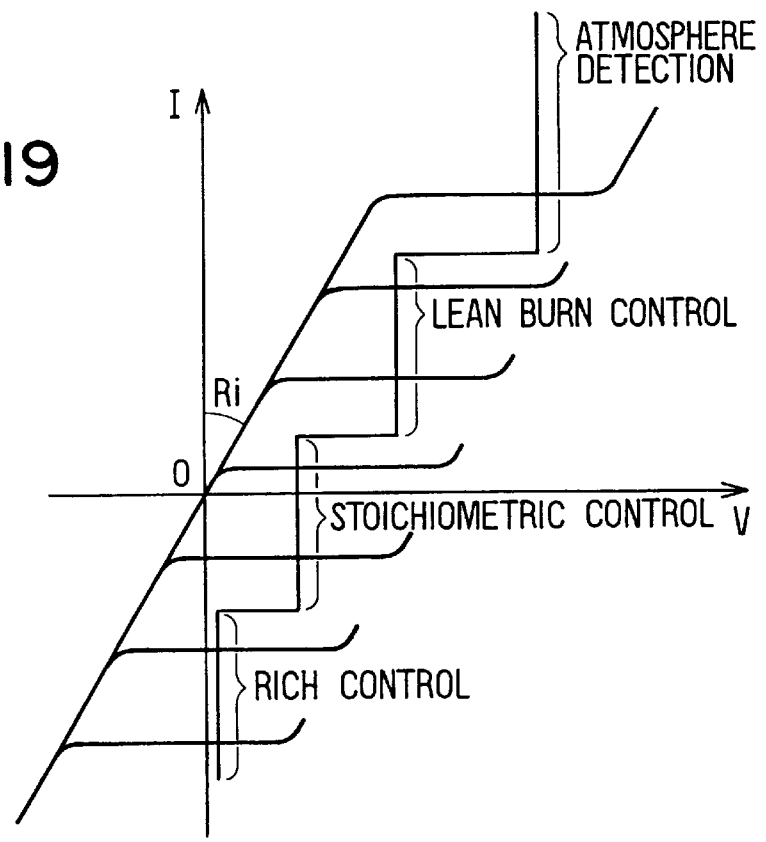
FIG. 19 is a V-I characteristic diagram showing the applied-voltage characteristic line according to the further embodiment.

(1) As shown in FIG. 19, in the V-I characteristic diagram of the A/F sensor 30, a characteristic line Lb which stepwisely varies may be set. In FIG. 19, the rich control region, the stoichiometric control region, the lean burn control region and the atmosphere detection region, for example, have a portion where the applied-voltage has a fixed value, and this figure lacks a portion where the respective regions are connected with a predetermined slope as shown in FIG. 8. In this case, the object of the present invention can also be attained. in this case, it may be arranged such that a plurality of voltage power sources, corresponding to the portions where the applied-voltage has a fixed value, for example, are prepared, and the voltage power sources are changed by switching means in accordance with the air-fuel ratio (sensor current value) at times. This construction removes complicated operation processing by the microcomputer 20, to reduce operational load, and reduces costs.

(2) In the above respective embodiments, when the applied-voltage is varied at a predetermined change speed, the changing operation is performed based on the resolution (5 mV/LSB) of the D/A converter 21. For this reason, regarding the voltage change amount ΔV less than the resolution of the D/A converter 21, the voltage value is held without any change (FIGS. 6 and 7). However, if a construction which linearly varies the voltage value with a high resolution is used, a slight amount of voltage change can be made, and the applied-voltage can be controlled to always correspond with the target applied-voltage value VT. In this case, the processing at steps 209, 212 and 216 in FIG. 7 is changed as "VR=VR+ΔV (ΔV corresponds to the shortage of the voltage change)".

(3) As the condition to variably set the applied-voltage change speed, as well as the sensor current value I and the voltage change amount ΔV, the following constructions as shown in FIGS. 20 to 26 may be employed.

Figure 20:
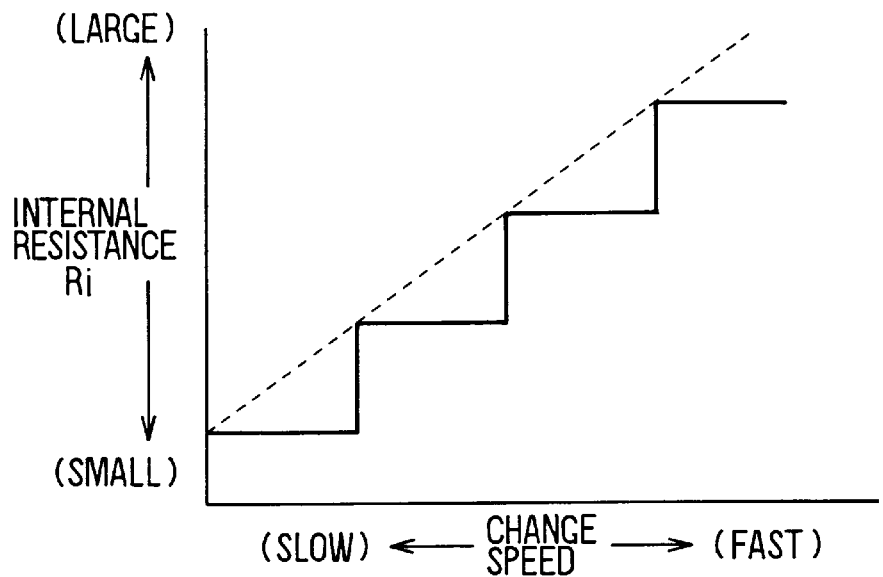
FIG. 20 is a graph showing the relation between the applied-voltage change speed and the internal-resistance.

As shown in FIG. 20, the applied-voltage change speed is variably set in accordance with the internal-resistance Ri of the A/F sensor 30. In this case, as the internal-resistance Ri increases, the change speed is increased while as the internal-resistance Ri decreases, the change speed is reduced. The solid line in FIG. 20 indicates a case where the change speed is stepwisely varied in accordance with the resolution of the D/A converter; the broken line indicates a case where the change speed is linearly varied.

Figure 21:
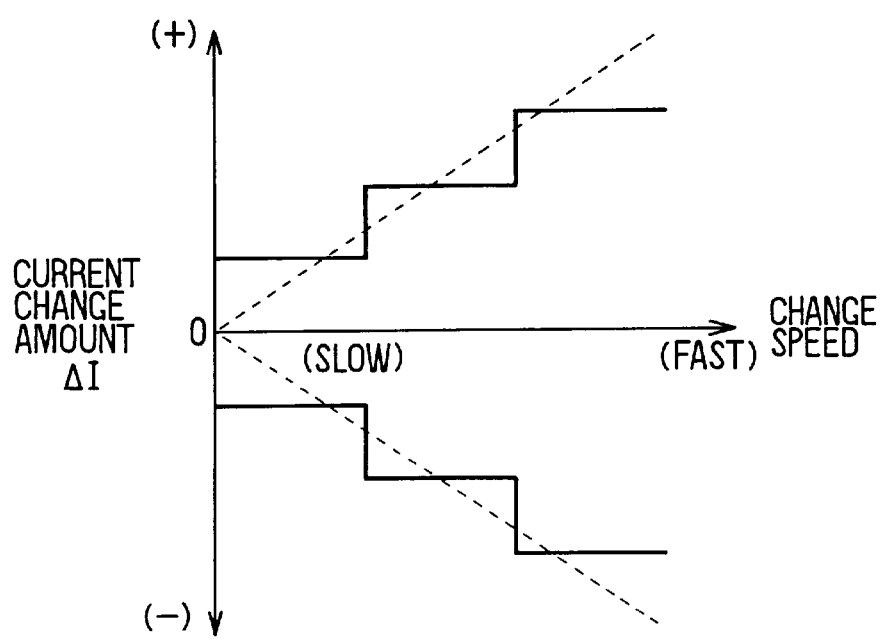
FIG. 21 is a graph showing the relation between the applied-voltage change speed and the current change amount.

As shown in FIG. 21, the applied-voltage change speed is variably set in accordance with the change amount ΔI of the sensor current value. In this case, as the change amount ΔI decreases, the change speed is reduced, while as the change amount ΔI increases toward the positive or negative side, the change speed is increased. In FIG. 21, the solid line indicates a case where the change speed is stepwisely varied in accordance with the resolution of the D/A converter; the broken line indicates a case where the change speed is linearly varied.

Figure 22:
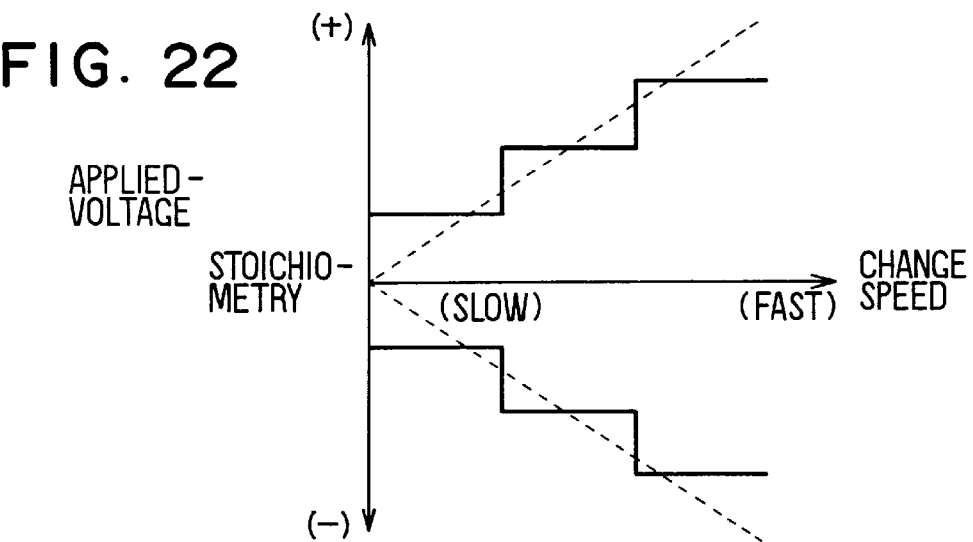
FIG. 22 is a graph showing the relation between the applied-voltage change speed and the applied-voltage value with a stoichiometric voltage as a reference.

As shown in FIG. 22, the applied-voltage change speed is variably set in accordance with the present applied-voltage value VR, with the applied-voltage at the stoichiometric ratio as a reference. In this case, as the applied-voltage value VR approaches to to the stoichiometric voltage, the change speed is reduced, while as the applied-voltage value VR moves away from the stoichiometric voltage, the change speed is increased. In FIG. 22, the solid line indicates a case where the change speed is stepwisely varied in accordance with the resolution of the D/A converter; the broken line indicates a case where the change speed is linearly varied.

Figure 23A:
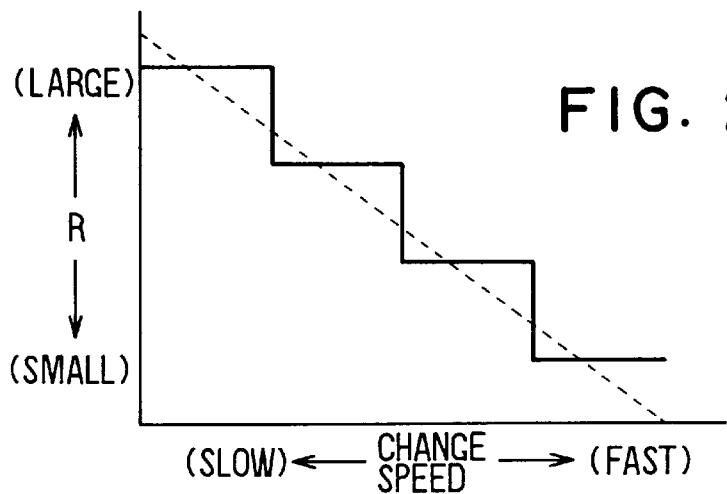
FIG. 23A is a graph showing the relation between the applied-voltage change speed and the angle at the turning point of the applied-voltage characteristic line.
Figure 23B:
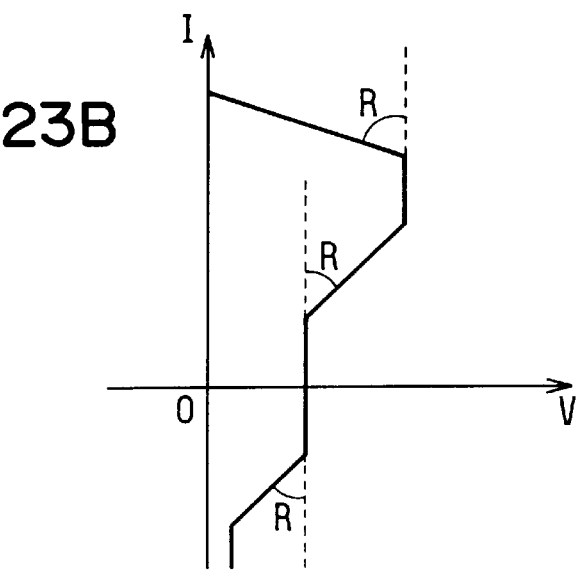
FIG. 23B is a V-I characteristic diagram showing the angle at the turning point of the applied-voltage characteristic line.

As shown in FIGS. 23A and 23B, the applied-voltage change speed is variably set in accordance with the slope of the applied-voltage characteristic line (angle R at the turning point). In this case, as the angle R of the applied-voltage characteristic line increases, the change speed is reduced, while as the angle R of the applied-voltage characteristic line decreases, the change speed is increased. In FIGS. 23A and 23B, the solid line indicates a case where the change speed is stepwisely varied in accordance with the resolution of the D/A converter; the broken line indicates a case where the change speed is linearly varied.

Figure 24:
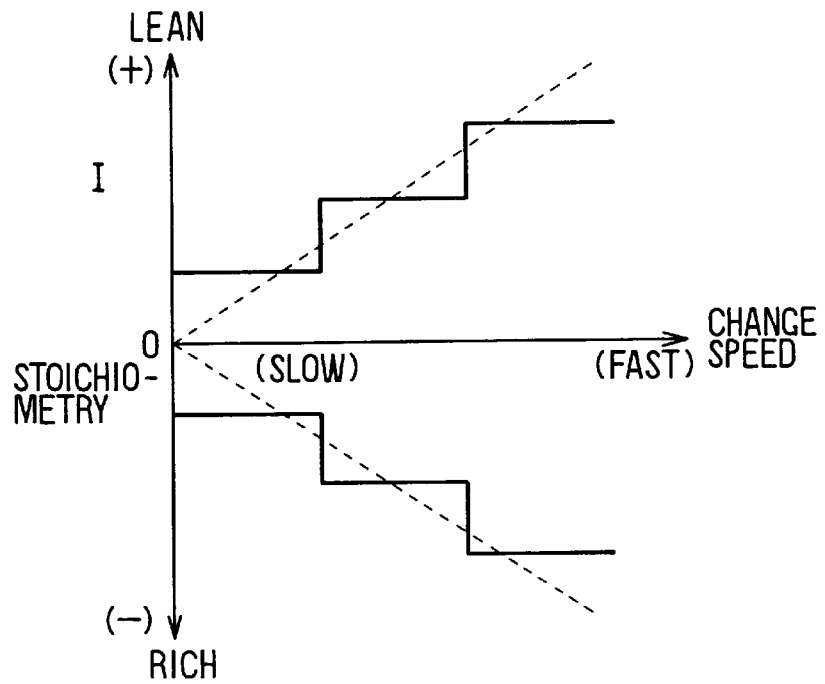
FIG. 24 is a graph showing the relation between the applied-voltage change speed and the sensor current value.
Figure 25:
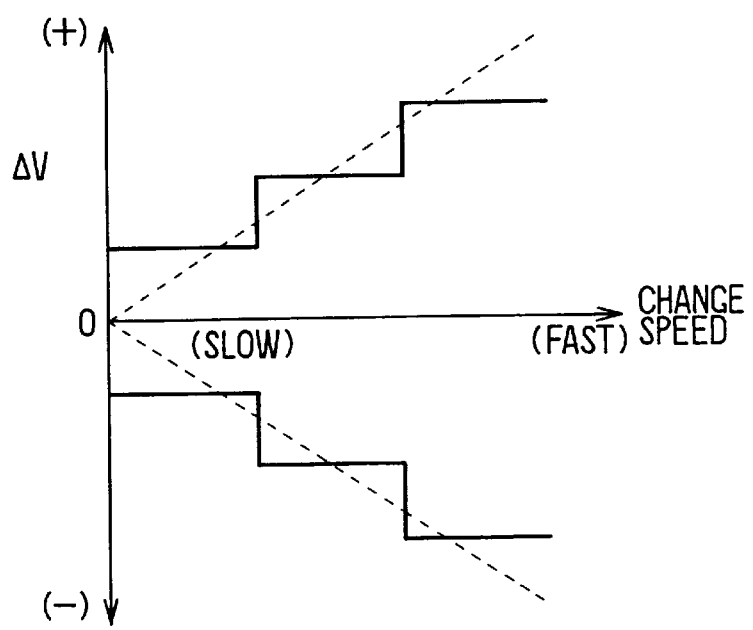
FIG. 25 is a showing the relation between the applied-voltage change speed and the voltage change amount.

The relation between the sensor current value I or the voltage change amount ΔV, and the applied-voltage change speed can be represented in graphs as shown in FIGS. 24 and 25. In these figures, the solid line indicates cases where the change speed is stepwisely varied in accordance with the resolution of the D/A converter; the broken line indicates a case where the change speed is linearly varied.

According to these constructions, the applied-voltage change speed can be set with higher precision, thus, more precise air-fuel ratio detection can be realized. Further, the response characteristics upon air-fuel ratio detection can be improved. In the above conditions, a condition to set the applied-voltage change speed is used depending on the designing idea at times, however, in any case, appropriate setting can be realized. Further, the air-fuel ratio detection precision can be further increased in a desired region by combining the above plural conditions.

(4) In the above embodiments, regarding the stoichiometric control region, the lean burn control region, the atmosphere detection region and the rich control region, the change rate of the voltage applied to the A/F sensor 30 is reduced, however, it may be arranged such that the change rate is reduced only in the stoichiometric control region, for example. In brief, only if the change rate of the voltage applied to the A/F sensor 30, in at least one specific region, is reduced to be less than that in other regions, the subject matter of the present invention can be realized. Further, as the above regions require high air-fuel ratio detection precision, the applied-voltage characteristic line is vertical to the axis V as shown in FIG. 8, for example. However, in these regions, it is not necessary that the characteristic line is vertical to the axis V, but the line has a slight slope. In brief, in the above regions require high air-fuel ratio detection precision, the change rate of the applied-voltage must only be less than that in other regions.

Figure 26:
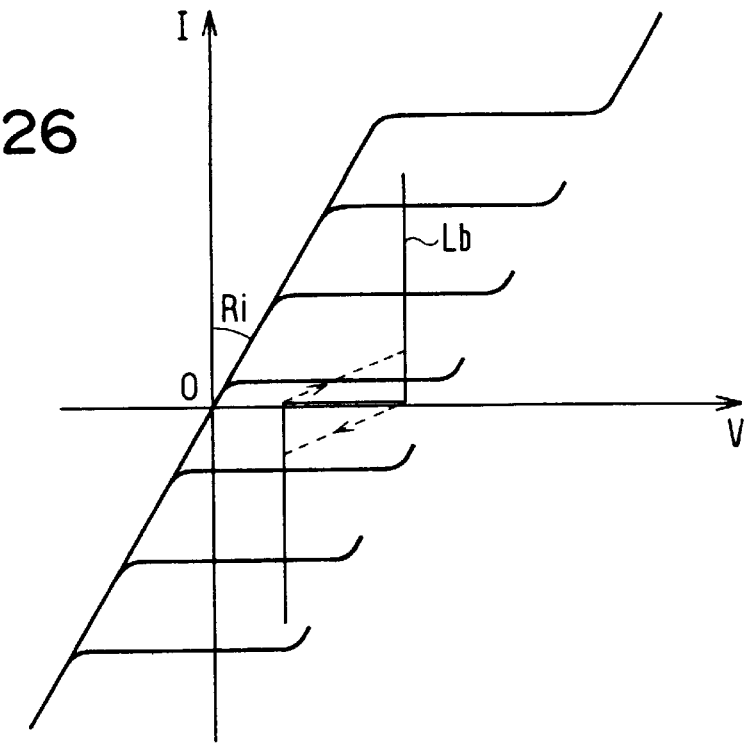
FIG. 26 is a V-I characteristic diagram showing the applied-voltage characteristic line according to the still further embodiment.

(5) As shown in FIG. 26, the applied-voltage characteristic line Lb is set for varying the applied-voltage value in a switching manner in accordance with rich or lean region. In this case, on the characteristic line Lb in FIG. 26, the applied-voltage seems to abruptly vary around the stoichiometric ratio; however, by reducing the applied-voltage change speed, the applied-voltage varies as represented with the broken line in FIG. 26, which prevents the inconvenience that the precision of air-fuel ratio detection is degraded due to abrupt change of the applied-voltage.

(6) The sensing element internal-resistance and the sensing element temperature of the A/F sensor 30 are in close relation to each other; specifically, as the sensing element temperature increases, the sensing element internal-resistance decreases, while as the sensing element temperature decreases, the sensing element internal-resistance abruptly increases. Then, in the above embodiments, the sensing element internal-resistance may be replaced with the sensing element temperature. The sensing element temperature may be detected by using a thermoelectric couple, radiation thermometer or the like.

(7) The above embodiments are implemented by using the cup-shaped A/F sensor (limit-current air-fuel ratio sensor), however, the present invention may be embodied by using a layered A/F sensor. In such case, the operation and effects as described above can be obtained.

(8) In the above embodiments, the present invention is applied to the A/F sensor for detecting the oxygen concentration (air-fuel ratio) in an exhaust gas of a vehicle gasoline engine. However, the present invention may be applied to other internal combustion engines such as a diesel engine and a CNG (natural gas) engine. Further, the application range of the present invention is not limited to the vehicle A/F sensor, but the application range can be widened for other sensors. For example, the present invention can be easily embodied as an oxygen concentration sensor which detects the oxygen concentration in an exhaust gas of a stationary internal combustion engine such as a co-generator engine.

What is claimed is:

1. An air-fuel ratio detection method comprising the steps of:

applying a reference voltage to an air-fuel ratio sensor which changes for outputting a current signal indicative of a detected air-fuel ratio in respectively corresponding different detection regions where each detection region has a characteristic rate of change for the reference voltage in that region; and reducing the rate of change of the voltage applied to the air-fuel ratio sensor in at least one specific air fuel ratio region;

wherein the specific region includes an air-fuel ratio feedback control region in which an air-fuel ratio is feedback-controlled to a target air-fuel ratio in response to an air-fuel ratio detected by the air-fuel ratio sensor.

2. An air-fuel ratio detection method as in claim 1, wherein the specific air-fuel ratio region includes a stoichiometric ratio peripheral region.

3. An air-fuel ratio detection method as in claim 1, wherein the specific region includes a region where the air-fuel ratio sensor outputs a fixed current for a range of applied voltage.

4. An air-fuel ratio detection method as in claim 1, wherein the voltage applied to the air-fuel ratio sensor has a fixed value in the specified region.

5. An air-fuel ratio detection method as in claim 1, wherein the specified region is variably set in correspondence with detected internal-resistance of the air-fuel ratio sensor.

6. An air-fuel ratio detection method comprising the steps of:

applying a reference voltage to an air-fuel ratio sensor which changes for outputting a current signal indicative of detected air-fuel ratio in respectively corresponding different detection ranges where each detection range has a characteristic speed of change for the reference voltage in that range varying the speed of change of the voltage applied to the air-fuel ratio sensor.

7. An air-fuel ratio detection method as in claim 6, wherein the speed of change of the reference voltage is varied in accordance with at least one of an incremental magnitude of change in voltage and a time period between voltage changes.

8. An air-fuel ratio detection method as in claim 6, wherein the speed of change is set to correspond to each of plural predetermined air-fuel ratio detection regions or in accordance with a detected current value.

9. An air-fuel ratio detection method as in claim 6, wherein the speed of change of the voltage is set in accordance with a difference between a target voltage and the voltage actually applied.

10. An air-fuel ratio detection method as in claim 6, wherein the speed of change of the voltage is set in accordance with internal-resistance of the air-fuel ratio sensor.

11. An air-fuel ratio detection method as in claim 6, wherein the speed of change of the voltage is set in accordance with an incremental amount of change in the current signal of the air-fuel ratio sensor.

12. An air-fuel ratio detection method as in claim 6, wherein the speed of change of the voltage is set in accordance with a present value of the actually applied voltage.

13. An air-fuel ratio detection method as in claim 6, wherein the speed of change of the voltage is set in accordance with the slope of a characteristic line on a voltage-current plot of the air-fuel ratio sensor.

14. An air-fuel ratio detection method as in claim 6, further comprising the step of:

using the air-fuel ratio detected by the air-fuel ratio sensor to feedback control the air-fuel ratio to a target air-fuel ratio, wherein the speed of change of the voltage is made faster than a previous speed of change in the middle of a feedback control range, when atmosphere detection is performed using the air-fuel ratio sensor.

15. An air-fuel ratio detection method as in claim 6 wherein the speed of change of the voltage is faster during times of non-feedback control of the air-fuel ratio than during times of feedback control of the air-fuel ratio.

16. An air-fuel ratio detection method as in claim 6 wherein the speed of change of the voltage is slower when the air-fuel ratio is being feedback controlled as compared to other air-fuel ratio controller in a leaner air-fuel ratio region.

17. An air-fuel ratio detection method comprising the steps of:

applying a voltage to an air-fuel ratio sensor which changes for outputting a current signal corresponding to an air-fuel ratio in a detection object gas;

varying in at least one specific region, where each specific region has a characteristic speed of change for the reference voltage in that region, the speed of change of the voltage applied to the air-fuel ratio sensor to be less than the speed of change in other regions during at least some predetermined conditions; and variably setting the speed of voltage changes sequentially when the voltage applied to the air-fuel sensor is varied.

18. An air-fuel ratio detection method as in claim 17, further comprising the step of:

using the air-fuel ratio detected by the air-fuel ratio sensor to feedback control the air-fuel ratio to a target air-fuel ratio, wherein the predetermined conditions includes conditions where the target air-fuel ratio is set, and the speed of change of the voltage is reduced to be slower than that in other conditions corresponding to regions of a characteristic V-I graph for the sensor that are adjacent to a region therein corresponding to said predetermined conditions.

* * * * *